United States Patent
Stone et al.

(10) Patent No.: US 8,820,135 B2
(45) Date of Patent: Sep. 2, 2014

(54) AUTO CALIBRATION / VALIDATION OF OXYGEN SENSOR IN BREATHING APPARATUS

(75) Inventors: William C. Stone, Del Valle, TX (US); Nigel Jones, New Market, MD (US)

(73) Assignee: Poseidon Diving Systems AB, Vastra Frolunda (SE)

( * ) Notice: Subject to any disclaimer, the term of this patent is extended or adjusted under 35 U.S.C. 154(b) by 1161 days.

(21) Appl. No.: 12/740,181

(22) PCT Filed: Oct. 29, 2008

(86) PCT No.: PCT/SE2008/051231
§ 371 (c)(1),
(2), (4) Date: Jan. 31, 2011

(87) PCT Pub. No.: WO2009/058083
PCT Pub. Date: May 7, 2009

(65) Prior Publication Data
US 2011/0114094 A1      May 19, 2011

Related U.S. Application Data

(60) Provisional application No. 61/000,741, filed on Oct. 29, 2007, provisional application No. 60/000,742, filed on Oct. 29, 2007.

(51) Int. Cl.
*A61M 16/12*     (2006.01)
*A62B 9/00*      (2006.01)
*B63C 11/12*     (2006.01)
*A61M 16/10*     (2006.01)

(52) U.S. Cl.
CPC ................. *A61M 16/12* (2013.01); *A62B 9/006* (2013.01); *A61M 2016/1025* (2013.01); *A61M 2205/702* (2013.01); *B63C 11/12* (2013.01)
USPC .......... 73/1.06; 128/204.22; 702/24; 702/100

(58) Field of Classification Search
CPC ..................... A61M 16/12; A61M 2016/1025; A61M 2016/122; A61M 2016/203; A61M 2202/0208; A61M 2205/17; A61M 2205/502; A61M 2205/702; A62B 9/006; B63G 11/24
USPC .......... 73/1.06–1.07; 128/204.22; 702/24, 100
See application file for complete search history.

(56) References Cited

U.S. PATENT DOCUMENTS

| 4,273,120 A | 6/1981 | Oswell |
| 4,516,424 A | 5/1985 | Rowland |

(Continued)

FOREIGN PATENT DOCUMENTS

| CA | 2 564 999 | 11/2005 |
| DE | 29 710 307 | 9/1997 |

(Continued)

OTHER PUBLICATIONS

International Search Report for PCT/SE2008/051231, mailed Jan. 28, 2009.

(Continued)

*Primary Examiner* — Thomas P Noland
(74) *Attorney, Agent, or Firm* — Nixon & Vanderhye P.C.

(57) ABSTRACT

A method for operating an oxygen sensor arrangement senses the oxygen in a breathing loop of a breathing apparatus. The sensor arrangement includes a primary oxygen sensor to measure the oxygen in the breathing loop, a secondary oxygen sensor to measure the oxygen in the breathing loop, and a control arrangement to obtain measures from the oxygen sensor. A test channel arrangement provides a first gas having a first fraction of oxygen from a first gas supply to the primary oxygen sensor at a position adjacent to the primary oxygen sensor. A test valve arrangement opens and closes the flow of the first gas through the test channel arrangement. The control arrangement actuates the first test valve arrangement to provide an amount of the first gas to the primary oxygen sensor via the test channel arrangement and obtain measures from the primary and secondary oxygen sensors.

15 Claims, 19 Drawing Sheets

(56) References Cited

U.S. PATENT DOCUMENTS

| | | | |
|---|---|---|---|
| 4,964,404 A * | 10/1990 | Stone | 128/204.22 |
| 5,094,235 A * | 3/1992 | Westenskow et al. | 128/204.22 |
| 5,127,398 A | 7/1992 | Stone | |
| 5,503,145 A * | 4/1996 | Clough | 128/204.22 |
| 6,003,513 A * | 12/1999 | Readey et al. | 128/202.22 X |
| 6,279,574 B1 | 8/2001 | Richardson et al. | |
| 6,470,885 B1 * | 10/2002 | Blue et al. | 128/204.18 |
| 6,520,180 B1 * | 2/2003 | Sahmkow et al. | 128/204.22 X |
| 6,712,071 B1 | 3/2004 | Parker | |
| 6,817,359 B2 * | 11/2004 | Deas et al. | |
| 7,353,824 B1 * | 4/2008 | Forsyth et al. | 128/204.22 |
| 8,302,603 B1 * | 11/2012 | Weber | |
| 8,424,522 B2 * | 4/2013 | Sieber | 128/204.22 |
| 2003/0127133 A1 | 7/2003 | Kim | |
| 2003/0188745 A1 | 10/2003 | Deas et al. | |
| 2005/0247311 A1 * | 11/2005 | Vacchiano et al. | |
| 2006/0201508 A1 * | 9/2006 | Forsyth et al. | 128/204.26 |
| 2007/0235030 A1 | 10/2007 | Teetzel et al. | |
| 2009/0250062 A1 | 10/2009 | Reynolds | |
| 2011/0041848 A1 * | 2/2011 | Stone et al. | |
| 2011/0073111 A1 | 3/2011 | Stone et al. | |

FOREIGN PATENT DOCUMENTS

| | | |
|---|---|---|
| DE | 100 14 959 | 5/2001 |
| GB | 2 208 203 | 3/1989 |
| GB | 2 340 760 | 3/2000 |
| GB | 2 404 593 | 2/2005 |
| WO | WO 99/04858 | 2/1999 |
| WO | WO 2005107390 A2 * | 11/2005 |
| WO | WO 2007/126317 | 11/2007 |
| WO | WO 2008/080948 | 7/2008 |

OTHER PUBLICATIONS

Written Opinion of the International Searching Authority for PCT/SE2008/051231, mailed Jan. 28, 2009.
Bailey et al. "Performance of Diving Equipment" Health and Safety Laboratory, Copyright 2006, pp. i-vi & 1-53.
International Search Report for PCT/SE2008/051226, mailed Jan. 23, 2009.
Written Opinion of the International Searching Authority for PCT/SE2008/051226, mailed Jan. 23, 2009.
Office Action mailed Jan. 7, 2013 in U.S. Appl. No. 12/740,208.
Office Action mailed Jul. 31, 2013 in U.S. Appl. No. 12/740, 208.
Office Action mailed Jun. 20, 2013 in U.S. Appl. No. 12/740,194.
Final Office Action mailed Dec. 19, 2013 in U.S. Appl. No. 12/740,194.
International Search Report for PCT/SE2008/051229, mailed Jan. 28, 2009.
Written Opinion of the International Searching Authority for PTC/SE2008/051229, mailed Jan. 28, 2009.

* cited by examiner

AUTO CALIBRATION / VALIDATION OF OXYGEN SENSOR IN BREATHING APPARATUS

This application is the U.S. national phase of International Application No. PCT/SE2008/051231, filed 29 Oct. 2008, which designated the U.S. and claims the benefit of U.S. Provisional Appln. No. 61/000,741, filed 29 Oct. 2007, and U.S. Provisional Appln. No. 60/000,742, filed 29 Oct. 2007, the entire contents of each of which are hereby incorporated by reference.

TECHNICAL FIELD

The present invention relates to breathing apparatuses and the control of oxygen in such breathing apparatuses.

BACKGROUND

It is well known to those skilled in the art that breathing apparatuses such as fully closed-cycle breathing apparatuses and similar—e.g. the specific sub-genre known as fully closed-cycle underwater breathing apparatus (CCUBA) or alternatively known as "closed-circuit rebreathers" or "CCR"—offer distinct advantages over the more common open-circuit breathing apparatuses such as e.g. Self-Contained Underwater Breathing Apparatuses (SCUBA) and the like. It should be emphasised that even if the text herein may focus on closed-cycled breathing apparatuses for diving purposes the same or similar advantages applies mutatis mutandis for closed-cycled breathing apparatuses in general and other breathing apparatuses wherein the amount of oxygen in the breathing gas has to be controlled.

Advantages provided by closed-cycle breathing apparatuses and similar are e.g. reduced bubble noise, extremely high gas usage efficiency, and optimized breathing gas composition etc. These and other advantages of closed-cycled breathing apparatuses such as CCRs derive from the fact that the exhaled breathing gas is recycled, filtered of carbon dioxide, replenished with oxygen, and returned to the diver for breathing again. The reduced bubble noise and the increased gas efficiency of a CCR both result from the fundamental function of recycling the breathing gas. The optimized breathing gas composition results from the fact that the oxygen control system of a CCR maintains a substantially constant partial-pressure of oxygen (rather than a constant fraction of oxygen, as in conventional open-circuit breathing apparatuses such as SCUBA and the like).

The partial pressure of a gas is a function of the fraction of the gas multiplied by the ambient pressure. As a diver descends and the depth increases, the ambient pressure also increases. Thus, for a given fraction of oxygen, the partial pressure increases as the depth increases. If the oxygen partial pressure exceeds a certain threshold (approximately 1.4 bar) the high concentration of oxygen and the risk of hyperoxia-induced seizure and other "oxygen toxicity" symptoms is considered unsafe for the diver. For example, the maximum safe depth at which a diver can breathe a mixture containing 50% oxygen is about 18 meters. On the other hand, the lower the oxygen concentration, the greater the concentration of non-oxygen gas constituents, such as nitrogen or helium. It is these non-oxygen components of the breathing mixture that lead to problems of decompression sickness (DCS), also known as "the bends", which include symptoms ranging from pain in the joints, to paralysis, to death. To maximize the amount of time that can be safely spent at any given depth, the non-oxygen portions of the breathing gas should be kept to a minimum; which means that the oxygen should be kept to its maximum safe limit at all points during the dive.

Thus, the advantage of CCR over conventional open-circuit SCUBA in terms of optimized breathing gas composition results from the fact that a CCR can maintain the maximum safe partial pressure of oxygen (PO2) throughout all depths of a dive, thereby minimizing the concentration of non-oxygen gas constituents—leading to increased allowed time at any give depth and/or reduced risk of DCS.

But this advantage comes at a cost. Whereas the breathing mixture for a conventional open-circuit SCUBA diver is fixed based on the composition of the gas in the supply cylinder, the breathing mixture in a CCR is dynamic. Although it is this dynamic mixture capability that affords the CCR one of its primary advantages, a failure of the oxygen control system can be extremely dangerous. A malfunction that allows the PO2 to get too high places the diver at risk of a hyperoxia-induced seizure, which would almost certainly cause the diver to drown. A malfunction that allows the PO2 to get too low may lead to hypoxic-induced blackout, causing the diver to drown and/or suffer severe brain damages. Therefore, perhaps the most critical aspect of any CCR design involves the reliability of the oxygen control system.

Most modern CCRs incorporate one or more electronic oxygen sensors that directly measure the PO2 of the breathing gas. Most such sensors involve a galvanic reaction that produces a voltage output that is proportional to the concentration of the oxygen exposed to the sensor. Electronic systems interpret the signals from the oxygen sensor(s) to control a valve connected to an oxygen supply. When the oxygen sensors detect a PO2 below a certain "setpoint" threshold, the valve is opened and a small amount of oxygen is injected into the breathing gas. The reliability of the oxygen sensors, therefore, is of paramount importance for ensuring a safe breathing gas mixture when using a CCR.

There are a number of ways that oxygen sensors—considered by most experienced CCR divers as the weakest link in the oxygen control system—can fail (i.e., provide false readings), e.g. due to faulty calibration, sensor failure or condensation etc.

In the exemplifying discussions that follow we will assume a commonly available galvanic oxygen sensor (essentially a fuel cell that produces voltage output in response to the PO2 level) that is widely in use in CCR apparatus. However, the following discussions apply mutatis mutandis to all sensors that produce an output signal proportional to PO2 or similar for any other gas.

Calibration

All galvanic oxygen sensors must be calibrated to ensure accurate readings. If a sensor falls out of proper calibration the electronic control system of a CCR will misinterpret the readings. A calibration process typically involves exposing the sensors to one or more known gas mixtures at a known ambient pressure, and deriving calibration constants to the electronic logic that interprets the sensor readings. Calibration is typically conducted manually or semi-automatically prior to the dive, but is sometimes only done periodically. Calibration constants can be recorded incorrectly if the calibration gas mixture deviates from expected (e.g., if the calibration process assumes a mixture of 100% oxygen when a contaminated calibration gas is actually only 80% oxygen), if the ambient pressure is not properly taken into account, if the sensor fails in certain ways as described below, and/or if the user performs the calibration process incorrectly. Attempts to mitigate these problems have included automated calibration routines as part of the standard pre-dive process, incorporation of ambient pressure sensors into the calibration process, and testing against threshold values intended to detect calibration errors.

Sensor Failure by Exhaustion or Similar

Galvanic oxygen sensors eventually fail either through exhaustion of their chemical reaction or other age related degradation of active sensing elements and/or from a host of other environmental and user-caused effects (e.g. abuse, improper use). In many cases, a sensor will simply fail to generate sufficient output voltage at the time of calibration, and will be identified. In other cases, however, a sensor can perform normally up to a certain point, but deviate significantly from linearity in output voltage once the oxygen concentration exceeds a certain value. For example, a sensor could perform normally up to an oxygen concentration of 1.1 bar partial pressure, but then fail to produce a correspondingly higher output voltage at higher oxygen concentrations. Because the calibration process of most CCR systems uses 100% oxygen at ambient pressure (i.e, 1 bar partial pressure) in a pre-dive calibration, the calibration process may appear to complete correctly, but the system may not be able to properly interpret readings when the sensor is exposed to oxygen partial pressures above 1 bar.

Sensor Failure by Condensation or Similar

Moreover, one of the most common modes of oxygen sensor failure involves condensation. The breathing gas in a CCR is humidified to near-saturation when the gas is exhaled from the diver's lungs. In most cases, ambient water temperature is cooler than body core temperature, so as the breathing gas is cooled in the CCR breathing loop, liquid condensation inevitably forms. As a consequence, the inside walls of the CCR breathing pathways are typically dripping wet with condensation after a short period of time. The total volume of condensate can exceed several tens of millilitres per hour of dive time. This condensation can affect the oxygen sensor and cause erroneous readings. It can also lead to premature failure of the sensor. In some circumstances, a thin film of condensate can form across the active sensing face of the oxygen sensor (frequently a metal mesh or hydrophobic membrane), trapping a tiny pocket of gas against the sensor that is isolated from the breathing gas mixture. This is among the most dangerous forms of oxygen sensor failure, because it provides a false but plausible reading to the electronics, concealing the nature of the failure. For example, if the trapped pocket of gas has an oxygen concentration that is below a certain "setpoint" threshold, then the control system will continue to add oxygen to the breathing loop until the actual breathed PO2 reaches dangerously high levels. Conversely, if the trapped pocket of gas has a PO2 above the "setpoint" value, the control system will fail to add any oxygen at all, and the PO2 of the breathing gas will gradually diminish due to the diver's metabolic oxygen consumption, until hypoxic levels are reached and the diver blacks out.

Attempts to mitigate this problem include "water traps" and absorbent pads in the breathing loop designed to divert collected condensate away from the oxygen sensors; strategic placement of sensors in areas least likely to form condensation; placement of sensors on different planes to reduce the probability of multiple sensors collecting condensate simultaneously.

Even more importantly, almost all electronically-controlled CCR systems thus far developed attempt to safeguard against the consequences of failed oxygen sensors through the incorporation of triplex redundancy (that is, by incorporating three oxygen sensors in the CCR). This is i.a. based on the notion that if only one oxygen sensor is used, and it fails in a way that gives otherwise plausible readings, then there is no logical way to recognize that the sensor has failed. Similarly, if two sensors are used and one of them is giving a false reading, the control system can logically recognize a problem (unless both sensors fail in the same way), but cannot determine which sensor is correct and which has failed. With three oxygen sensors, so the conventional thinking goes, the system has "voting" logic. Assuming only one sensor fails at a time then the control system can be designed to interpret the two readings that agree within some pre-accepted tolerance as correct and thereby isolate the bad sensor reading.

Examples of breathing apparatuses that use three oxygen sensors and a "voting" logic or similar are disclosed in the patent documents U.S. Pat. No. 6,712,071 (Parker), GB 2404593 (Deas) and CA 2564999 (Straw).

Though ubiquitous among modern rebreather designs, the three-sensor approach to monitoring oxygen concentration in the breathing mixture is far from perfect. First, some more or less arbitrary threshold values must be established in order to carry out the voting logic. Because sensor readings can be slightly unstable in the chaotic breathing gas mixture of a CCR, a sensor must deviate from the other two sensors by a certain minimum threshold amount before it is considered suspect.

Then there is the question of what this threshold is measured against? For example, should the basis for the threshold comparison of one potentially errant sensor reading be the average value of the remaining two sensors, or the value of the sensor with the closest reading (i.e., the sensor giving the "middle" reading of the three) or perhaps something else?

Another problem with reliance upon the triple-redundant oxygen sensor system is the fact that sometimes two sensors fail the same way—often due to asymmetric condensate formation or because a user may have replaced one sensor with a fresh one and the other two are at the end of their useful life but may have exhibited in-range readings prior to the start of a dive (there are many such possibilities)—such that the apparently errant sensor reading is actually the correct reading. This mode of failure is particularly dangerous in that the control system actively ignores the true reading. Although this failure mode may seem unlikely, it has been documented on countless occasions in actual dive logs. Indeed, there have even been documented cases where all three sensors fail simultaneously such that all three give the same, but false reading. Other documented cases involve situations where no two sensors agree.

Once the threshold values and basis of comparison (voting logic algorithm) are determined, there is still the question of how best to adjust the oxygen control system in the event of an apparently failed sensor. Given two concordant values, and one errant value, should the control system simply ignore the errant value altogether and base its control logic on the average of the remaining two sensors? Or, should it base its control on the "middle" value of the three sensor readings—just in case the apparently errant sensor may be correct? Or, should additional logic be used such that the "setpoint" is adjusted dynamically, so that both the highest sensor value and the lowest sensor value are both kept within life-sustaining limits at all times? And what should the control system do in the even that no two oxygen sensors agree? Should it bias its logic to safeguard more rigorously against hypoxia, or hyperoxia?

Indeed, there are probably as many different answers to the questions and problems indicated above as there are people who have designed CCR oxygen control systems.

Although using three oxygen sensors and using sensors designed specifically for humid environments can mitigate some of the problems indicated above, all known CCR oxygen control systems are subject to failures due to one or more of the above problems. Hence, in view of the above there seems to be a need of improvements related to the control of oxygen in the breathing gas of a closed-cycle breathing apparatus and similar.

SUMMARY OF THE INVENTION

The present invention represents a new approach to oxygen control systems in closed-cycle breathing apparatuses such as CCRs and similar and other breathing apparatuses wherein the amount of oxygen in the breathing gas has to be controlled, e.g. continuously monitored. Other examples can e.g. be found in the medical area, e.g. such as medical ventilators and respirators of different kinds etc.

The control system involves automated active testing and/or monitoring of an oxygen sensor that is more reliable than the passive triple-redundancy control system that is currently in common use. The approach capitalizes on a repeated testing and monitoring technique and the availability of pure oxygen and/or a primarily non-oxygen gas supply (e.g., air), which are both typically available on almost all CCR systems. Here, it should be emphasised that even if the text herein may focus on closed-cycled breathing apparatuses for diving purposes the same or similar applies mutatis mutandis for other closed-cycled breathing apparatuses or similar.

For example, an oxygen control system according to an embodiment of the present invention incorporates two oxygen sensors (one may be designated as the "Primary Sensor", and the other may be designated as the "Secondary Sensor") and a minimum of three electronically controlled gas valves: two used to inject oxygen, and one used to inject "diluent" gas (i.e., a mixture containing primarily non-oxygen but nonetheless constituting a gas mixture that is directly breathable in open circuit mode within some regime of a planned dive—typically it is designed to be breathable at the maximum planned dive depth). The "diluent" gas supply may e.g. be air (~21% oxygen, ~79% nitrogen and other trace gases), but any breathable mixture containing at least some (known) oxygen fraction will serve the same purpose. It should be added that oxygen gas has a fraction of oxygen that is 1 or nearly 1 (i.e. 100% or nearly 100% oxygen). As indicated above, the it is preferred that the oxygen control system periodically validates the readings of the Primary Sensor using controlled direct injections of either oxygen or diluent (depending on the depth and the circumstances) and monitoring the response of the sensor to validate accurate readings. It is also preferred that these gas injections also serve the purpose of removing any condensation that may form on the face of the sensors, thus eliminating one of the common failure modes described above. It is also preferred that the Secondary Sensor is used to monitor the oxygen content of the breathing gas while the Primary Sensor is being validated, and also to safeguard against possible failure modes of the Primary Sensor validation system, e.g. possible leakage in the control valves that inject oxygen or diluent onto the primary sensor which would cause faulty oxygen readings.

Initial Sensor Calibration

Since it is preferred that the primary sensor in the present invention has direct access to both oxygen and known diluent mixtures (e.g., air) via electronically-controlled microvalves, the system is capable of calibrating itself without any input from the user and it is capable of performing the calibration with an exceedingly small volume of consumable gas, which is an important performance measure in CCR systems and which allows these systems to be substantially more compact than open circuit systems providing equivalent diving range at a given depth. Nor do preferred embodiments of the present invention require any reliance of proper user-initiated calibration routines or any interaction of the user at all. At initial power-up, the system will automatically inject a burst of pure diluent gas (e.g., air) directly on the primary Oxygen Sensor, reliably exposing it to a known low-oxygen mixture. If a diver is not breathing on the CCR breathing loop at the time of calibration, then a sufficient volume of diluent gas can be injected to also expose the nearby Secondary Oxygen Sensor. The same procedure applies to the oxygen supply mixture as well. These two known points provide a precise 2 point calibration for the primary oxygen sensor.

Although there may have been previous attempts to automatically calibrate oxygen sensors as part of the normal start-up routine in a CCR, typically these calibrations only apply to the pure oxygen portion of the calibration and typically they require a large wasteful volume of oxygen to adequately ensure that the sensors themselves are exposed to a reliably high concentration of oxygen. One reason for known calibration approaches being wasteful and inaccurate with regard to auto-calibration is that the same system used to add metabolic oxygen is the one used in the calibration. It is traditional industry practice to inject metabolic make up oxygen in a fashion that mixes the gas in the breathing loop long before reaching the oxygen sensors. Because of this, if one is using the metabolic oxygen valve for calibration purposes the entire breathing loop (as much as 7 liters in volume) must be completely flushed several times in order to approximate an good calibration. Even so, such loop-flushing procedures are never 100% complete and are subject to user intervention (e.g. setting a valve position wrong prior or during the calibration). Similarly, the breathing loop must then be manually completely flushed with air in order to achieve the 2-point calibration. Both actions require the interaction of the diver with the system and are therefore not truly automatic. Further, this approach is only possible on the surface prior to a dive; it cannot be used to detect a true sensor failure during a dive. Further, such an approach is subject to all of the above-described sensor failure and spoofing scenarios which could lead to a significant probability of an incorrect calibration.

Preferred embodiments of the invention described here—because of the availability of oxygen and diluent (e.g., air) directly applied to the primary Oxygen Sensor via the electronically-controlled Oxygen Test Valve and Diluent Test Valve, and the proximity of the Secondary Oxygen Sensor to the Primary Oxygen Sensor—are much more effective and efficient for establishing accurate calibration of the oxygen sensors prior a dive. Additional embodiments of the invention have been made even more reliable by:

1) incorporating threshold limits to detect when a sensor falls out of acceptable output voltage values at calibration time;
2) use of algorithmic analysis of a stored log of calibration values to detect calibration trends, alerting the user to a need to replace a sensor; and
3) clear "Do not Dive" indicators that prevent the user from operating the system in the event that the pre-dive calibration process does not complete successfully.

An additional benefit of the automatic pre-dive check as indicated above is that it can also serve as a pre-dive verification that the correct gas mixture (oxygen or diluent) is connected to the correct supply regulator (within calibration threshold tolerances of the sensors).

In-Dive Sensor Testing With Diluent Gas

Another new feature of embodiments of the oxygen control system described herein is the ability to monitor and test the function of oxygen sensors during the course of the dive—either at periodic time intervals, or in response to specific circumstances detected by the Electronic Control System. When desired, the system can automatically inject a small amount of diluent gas onto the Primary Oxygen Sensor, and then observe the resultant reading from the sensor as it is interpreted by the electronic control system. With an ambient pressure sensor and a known oxygen fraction in the diluent supply, the Primary Oxygen Sensor can be exposed to a known partial pressure of oxygen at any moment during the dive, and monitored to ensure that the sensor responds with the correct reading. Failure of this test can initiate an alert to the diver that the dive should be aborted immediately.

In-Dive Sensor Testing With Oxygen

Because embodiments of the system also has access to 100% oxygen and can inject it directly onto the Primary Oxygen Sensor, the system is also capable of testing the linearity of the sensor voltage output at partial pressures in excess of 1 bar (i.e., the maximum calibration value during pre-dive). For example, when the Electronic Control System detects via an ambient pressure sensor that the diver has reached a depth of 20 feet (6 m), where the ambient pressure is approximately 1.6 bar, a small burst of oxygen directly on the Primary Oxygen Sensor can ensure that the calibration constants apply reliably for readings at partial pressures well above 1.0 bar. Thus, if the system is set to maintain an oxygen partial pressure of 1.3 bar, there can be confidence in the reliability of the readings at that value, even though it is higher than the maximum pre-dive calibration value of 1.0 bar. As with the diluent injections, the volume of oxygen needed to be injected to perform this test is so small that it would not have a significant impact on the overall gas composition in the CCR breathing loop. Hence, embodiments of the invention described herein offer a full range sensor calibration extending beyond the typical calibration performed on the surface at 1 bar. Furthermore, this calibration can be performed in a fully automated fashion that is "transparent" to, and requires no interaction from, the user.

A Secondary Oxygen Sensor

The incorporation of a Secondary Oxygen Sensor into embodiments of the system adds to the reliability of the overall sensor monitoring system architecture in several ways. During periods when the Primary Oxygen Sensor is not being actively tested, the Secondary Oxygen Sensor can be compared to the Primary Oxygen Sensor to ensure concurrency of readings. If the readings are not concurrent, the system can be triggered to perform a test on the Primary Oxygen Sensor. If the discrepancy of readings was caused by condensation on the Primary Oxygen Sensor, the test itself may correct the problem. If the Primary Oxygen Sensor fails the test, the system can issue an abort alert, and initiate a test of the Secondary Oxygen Sensor, e.g. by increasing the volume of gas injected at the Primary Oxygen Sensor. If the Primary Oxygen Sensor passes the test, but the Secondary Oxygen Sensor is still providing inconsistent readings (e.g., if condensation has formed on the Secondary Oxygen Sensor, or if the Secondary Oxygen Sensor has failed for some other reason), then an abort alert can be issued to the diver. Another reason for incorporating a Secondary Oxygen Sensor that is not connected directly to the output from the Diluent Test Valve or the Oxygen Test Valve, is that it can serve as a "sentry" to safeguard against small leaks from either of the test valves. If there was a large leak of either of these valves, it is likely that the control logic of the Electronic Control System would recognize it immediately, and initiate an abort alert to the diver. However, if there was a very small leak in either of the test valves, a trickle of gas onto the Primary Oxygen Sensor might be such that it would bias the reading, but not so much that it could be detected by the Electronic Control System. The sensor would be functioning normally, and would pass all tests, but because the gas in immediate proximity to the sensor membrane is exposed to a contaminated gas mixture (not the actual breathing gas mixture) it would provide erroneous readings and lead to a malfunction of the oxygen control system. Malfunction in this sense meaning that the metabolic oxygen addition solenoid would fail to add oxygen in the event that the true PO2 dropped below the pre-set threshold for adding oxygen or, alternatively, that the metabolic oxygen addition solenoid would add oxygen when the true PO2 was within acceptable limits or higher than acceptable limits. Having a Secondary Oxygen Sensor that is not directly exposed to the gas coming from the test valves would result in detection of this failure mode due to discrepancy of readings between the two sensors (as described above). If the leak is so large that it causes contamination of the Secondary Oxygen Sensor, it would be large enough to detect by itself, and even still would not affect the Secondary Sensor as much as the Primary Oxygen Sensor, hence causing a (detectible) discrepancy in readings. Yet another reason for having a Secondary Oxygen Sensor is that it can be used to monitor the actual breathing gas while the Primary Oxygen Sensor is being tested. Whereas the Primary Oxygen Sensor is not exposed to the actual breathing mixture during tests, the Secondary Oxygen Sensor continues to monitor the breathing loop gas.

Oxygen Replenish Valve

Because oxygen replenishment is a normal function of a CCR oxygen control system, it would be unwise to use the Oxygen Test Valve for this purpose. Thus, the present invention utilizes a separate Oxygen Replenish Valve (or a plurality of valves) for injecting oxygen, intended to replenish that which is consumed by the diver, into a location on the breathing loop where it will not impact the oxygen sensor readings directly. The oxygen injected to replenish the metabolized oxygen would be adequately mixed with the breathing loop gas before it reaches either oxygen sensor.

A first embodiment of the present invention is directed to an oxygen sensor arrangement for sensing the oxygen in a breathing loop of a breathing apparatus. The oxygen sensor arrangement comprises: at least one primary oxygen sensor arranged to operatively measure the oxygen in the breathing loop, and at least a secondary oxygen sensor is arranged to operatively measure the oxygen in the breathing loop, and a control arrangement for obtaining measures from said oxygen sensor. A test channel arrangement is adapted to operatively provide a first gas having a first fraction of oxygen from a first gas supply to said primary oxygen sensor at a position adjacent to or directly adjacent to said primary oxygen sensor. At least a first test valve arrangement is arranged to operatively open and close the flow of said first gas through said test channel arrangement. The control arrangement is arranged to operatively actuate said first test valve arrangement so as to provide an amount of said first gas to said primary oxygen sensor via said test channel arrangement. The control arrangement is also arranged to operatively obtain measures from said primary and secondary oxygen sensors.

A second embodiment of the present invention, comprising the features of the first embodiment, is directed to an oxygen sensor arrangement wherein: the test channel arrangement is adapted to provide a second gas having a second fraction of oxygen from a second gas supply to said primary oxygen sensor at a position adjacent to or directly adjacent to said primary oxygen sensor. At least a second test valve arrangement is arranged to operatively open and close the flow of said second gas through said test channel arrangement. The control arrangement is arranged to operatively actuate said second test valve arrangement so as to provide an amount of said second gas to said primary oxygen sensor via said test channel arrangement.

A third embodiment of the present invention, comprising the features of the second embodiment, is directed to an oxygen sensor arrangement wherein: the test channel arrangement comprises a first test channel arrangement for providing said first gas from said first gas supply to said primary oxygen sensor at a first position adjacent to or directly adjacent to said primary oxygen sensor, and a second test channel arrangement for providing said second gas from said second gas supply to said primary oxygen sensor at a second position adjacent to or directly adjacent to said primary oxygen sensor.

A fourth embodiment of the present invention, comprising the features of the first embodiment, is directed to an oxygen sensor arrangement wherein: the control arrangement is arranged to operatively obtain at least one first test measure from said primary oxygen sensor when it is provided with an amount of said first gas.

A fifth embodiment of the present invention, comprising the features of the fourth embodiment, is directed to an oxygen sensor arrangement wherein: the control arrangement is arranged to operatively obtain at least one second test measure from said primary oxygen sensor when it is provided with an amount of said second gas.

A sixth embodiment of the present invention, comprising the features of the fifth embodiment, is directed to an oxygen sensor arrangement wherein: the control arrangement is arranged to operatively: calculate at least a first calibration point using said first test measure and at least using the known fraction of oxygen in the first gas, and calculate at least a second calibration point using said second test measure and at least using the known fraction of oxygen in the second gas, and generate a calibration curve for said primary oxygen sensor at least based on said first calibration point and said second calibration point.

A seventh embodiment of the present invention, comprising the features of the fourth or the fifth embodiment, is directed to an oxygen sensor arrangement wherein said control arrangement is arranged to operatively: obtain a validation point value using said first test measure or said second test measure, and obtain an expected value for the validation point value, at least using the known fraction of oxygen in the first gas or the known fraction of oxygen in the second gas, and determine if the validation point value deviates from the expected value more than a predetermined amount.

An eighth embodiment of the present invention, comprising the features of the sixth and the seventh embodiments, is directed to an oxygen sensor arrangement wherein said control arrangement is arranged to operatively: obtain the expected value for the validation point value by using the calibration curve so as to compensate for possible deviations in said primary oxygen sensor.

A ninth embodiment of the present invention, comprising the features of the fourth or the fifth embodiment, is directed to an oxygen sensor arrangement comprising at least one pressure sensor for measuring the ambient pressure affecting the breathing loop, wherein: the control arrangement is arranged to operatively obtain measures from said pressure sensor in connection with at least one of said first test measure or said second test measure, so as to provide the partial pressure of oxygen (PO2) for at least one of said first test measure or said second test measure.

A tenth embodiment of the present invention, comprising the features of any one of the first, the second or the third embodiment, is directed to an oxygen sensor arrangement wherein: said first oxygen sensor is arranged in a cavity that is in fluid communication with the breathing loop and that is provided with at least one output orifice for said test channel arrangement, which output orifice is arranged at a position adjacent to or directly adjacent to said oxygen sensor so that at least on of said first gas or said second gas can be operatively injected at an oblique angle with respect to the surface of the primary oxygen sensor.

An eleventh embodiment of the present invention, comprising the features of the first or the second embodiment, is directed to an oxygen sensor arrangement wherein said control arrangement is arranged to operatively obtain measures from the secondary oxygen sensor and the primary sensor when no test valve arrangements are actuated.

A twelfth embodiment of the present invention, comprising the features of the first or the second or the eleventh embodiment, is directed to an oxygen sensor arrangement wherein said control arrangement is arranged to operatively obtain a fitted calibration curve for said secondary oxygen sensor using measures operatively assembled from the secondary oxygen sensor and the primary sensor.

A thirteenth embodiment of the present invention, comprising the features of the twelfth embodiment, is directed to an oxygen sensor arrangement wherein said control arrangement is arranged to operatively obtain statistical correlation representation indicative of the correlation of the assembled measures with respect to the obtained fitted calibration curve.

A fourteenth embodiment of the present invention, comprising the features of the thirteenth embodiment, is directed to an oxygen sensor arrangement wherein said control arrangement is arranged to operatively issue an alert to the user if the statistical correlation representation is outside an allowable tolerance.

A fifteenth embodiment of the present invention, comprising the features of the eleventh embodiment, is directed to an oxygen sensor arrangement wherein: said control arrangement is arranged to operatively actuate at least one of said first test valve arrangement r said second test valve arrangement if the primary sensor measures deviates from the secondary oxygen sensor measures more than a predetermined amount.

A sixteenth embodiment of the present invention, comprising the features of the eleventh embodiment, is directed to an oxygen sensor arrangement wherein: said secondary oxygen sensor is arranged at a distance from the gas output of at least one of said first test valve arrangement or said second test valve arrangement, such that a gas leakage from at least one of said first test valve arrangement or said second test valve arrangement will cause the secondary sensor to operatively provide a different measure compared to the measure provided by the primary oxygen sensor.

A seventeenth embodiment of the present invention, comprising the features of the eleventh embodiment, is directed to an oxygen sensor arrangement wherein: the secondary oxygen sensor is arranged nearby the primary sensor so as to enable said control arrangement is arranged to operatively actuate at least one of said first test valve arrangement or said second test valve arrangement so as to validly expose the secondary oxygen sensor by gas having said first fraction of oxygen or said second fraction of oxygen.

An eighteenth embodiment of the present invention is directed to a method for sensing the oxygen in a breathing loop of a breathing apparatus wherein the method in an oxygen sensor arrangement comprises the steps of; actuating a first test valve arrangement so as to provide an amount of a first gas having a first fraction of oxygen via a test channel arrangement to a primary oxygen sensor at a position adjacent to or directly adjacent to said primary oxygen sensor.

A nineteenth embodiment of the present invention, comprising the features of the eighteenth embodiment, is directed to a method comprising the steps of: actuating a second test valve arrangement so as to provide an amount of a second gas having a second fraction of oxygen via said test channel arrangement to said primary oxygen sensor at a position adjacent to or directly adjacent to said primary oxygen sensor.

A twentieth of the present invention, comprising the features of the nineteenth embodiment, is directed to a method comprising the steps of providing said first gas through a first test channel arrangement to said primary oxygen sensor at a first position adjacent to or directly adjacent to said primary oxygen sensor, and providing said second gas through a second test channel arrangement to said primary oxygen sensor at a second position adjacent to or directly adjacent to said primary oxygen sensor.

A twenty first embodiment of the present invention, comprising the features of the eighteenth embodiment, is directed to a method comprising the steps of: obtaining at least one first test measure from said primary oxygen sensor when it is provided with an amount of said first gas.

A twenty second embodiment of the present invention, comprising the features of the twenty first embodiment, is directed to a method comprising the steps of obtaining at least one second test measure from said primary oxygen sensor when it is provided with an amount of said second gas.

A twenty third embodiment of the present invention, comprising the features of the twenty second embodiment, is directed to a method comprising the steps of calculating at least a first calibration point using said first test measure and at least using the known fraction of oxygen in the first gas, and calculating at least a second calibration point using said second test measure and at least using the known fraction of oxygen in the second gas, and generating a calibration curve for said primary oxygen sensor at least based on said first calibration point and said second calibration point.

A twenty fourth embodiment of the present invention, comprising the features of the twenty second embodiment, is directed to a method comprising the steps of obtaining a validation point value using said first test measure or said second test measure, and obtaining an expected value for the validation point value, at least using the known fraction of oxygen in the first gas or the known fraction of oxygen in the second gas, and determining if the validation point value deviates from the expected value more than a predetermined amount.

A twenty fifth embodiment of the present invention, comprising the features of the twenty third and the twenty fourth embodiments, is directed to a method comprising the steps of obtaining the expected value for the validation point value by using the calibration curve so as to compensate for possible deviations in said primary oxygen sensor.

A twenty sixth embodiment of the present invention, comprising the features of the twenty second or the twenty third embodiment, is directed to a method comprising the steps of obtaining measures the ambient pressure from a pressure sensor in connection with at least one of said first test measure or said second test measure, so as to provide the partial pressure of oxygen (PO2) for at least one of said first test measure or said second test measure.

A twenty seventh embodiment of the present invention, comprising the features of any one of the eighteenth or the nineteenth or the twentieth embodiment, is directed to a method comprising the steps of injecting said first gas or said second gas at an oblique angle with respect to the surface of the primary oxygen sensor.

A twenty eight embodiment of the present invention, comprising the features of the eighteenth or the nineteenth embodiment is directed to a method comprising the steps of obtaining measures from a secondary oxygen sensor and the primary sensor when no test valve arrangements are actuated.

A twenty ninth embodiment of the present invention, comprising the features of any one of the seventeenth, eighteenth or the nineteenth embodiment is directed to a method comprising the steps of obtaining a fitted calibration curve for said secondary oxygen sensor using measures operatively assembled from the secondary oxygen sensor and the primary sensor.

A thirteenth embodiment of the present invention, comprising the features of the twenty ninth embodiment is directed to a method comprising the steps of obtaining statistical correlation representation indicative of the correlation of the assembled measures with respect to the obtained fitted calibration curve.

A thirty first embodiment of the present invention, comprising the features of the thirtieth embodiment is directed to a method comprising the steps of issuing an alert to the user if the statistical correlation representation is outside an allowable tolerance.

A thirty second embodiment of the present invention, comprising the features of the twenty eighth embodiment, is directed to a method comprising the steps of actuating at least one of said first test valve arrangement or said second test valve arrangement if the primary sensor measures deviates from the secondary oxygen sensor measures more than a predetermined amount.

A thirty third embodiment of the present invention, comprising the features of the twenty eighth embodiment, is directed to a method comprising the steps of arranging the secondary oxygen sensor at a distance from the gas output of at least one of said first test valve arrangement or said second test valve arrangement, such that a gas leakage from at least one of said first test valve arrangement or said second test valve arrangement will cause the secondary sensor to operatively provide a different measure compared to the measure provided by the primary oxygen sensor.

A thirty fourth embodiment of the present invention, comprising the features of the twenty eighth embodiment, is directed to a method comprising the steps of arranging the secondary oxygen sensor nearby the primary sensor and actuating at least one of said first test valve arrangement or said second test valve arrangement so as to validly expose the secondary oxygen sensor by gas having said first fraction of oxygen or said second fraction of oxygen.

Further advantages of the present invention and embodiments thereof will appear from the following detailed description of the invention.

It should be emphasized that the term "comprises/comprising" when used in this specification is taken to specify the presence of stated features, integers, steps or components, but does not preclude the presence or addition of one or more other features, integers, steps, components or groups thereof.

It should also be emphasised that the methods defined in the appended claims may without departing from the present invention comprise further steps and/or the steps specified may be performed in another order than the order in which they appear in the claims.

DETAILED DESCRIPTION OF EMBODIMENTS

Basic Breathing Apparatus

Figure 1:
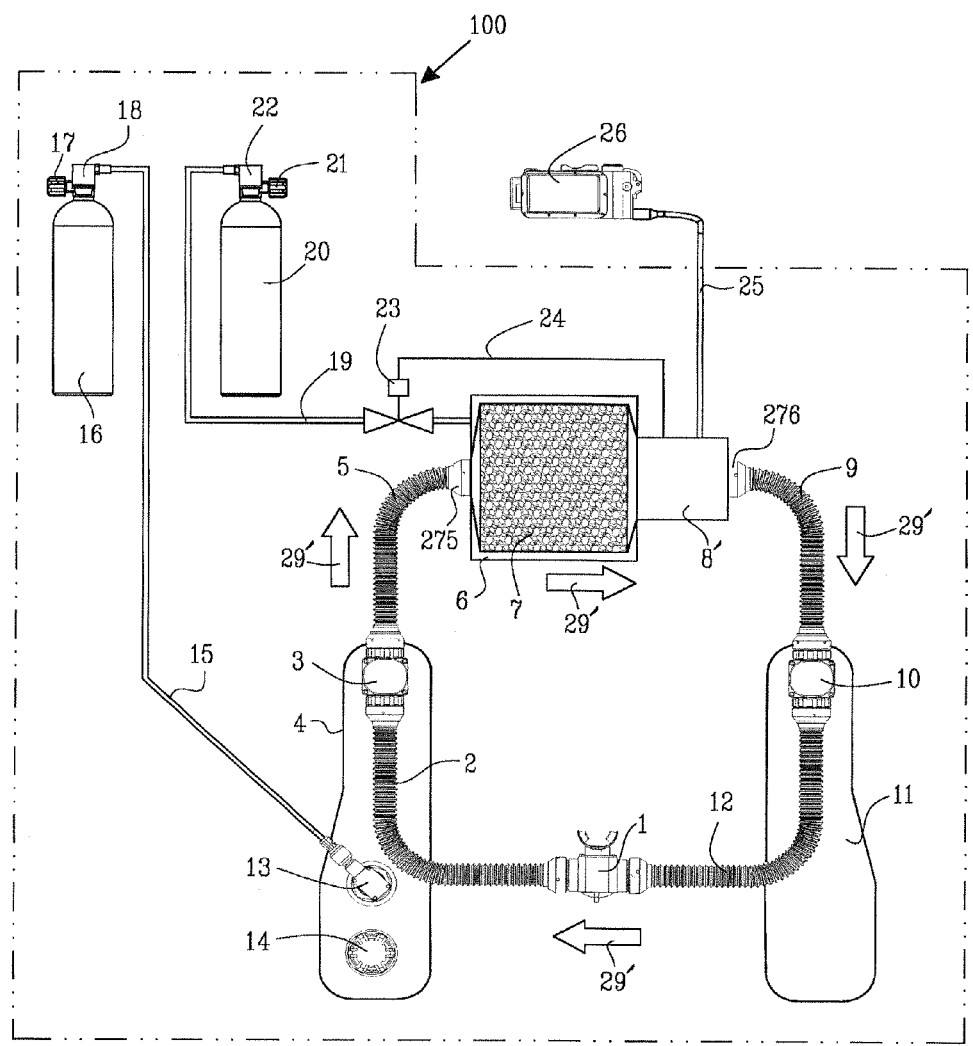
FIG. 1 shows in schematic mode an exemplifying breathing apparatus in the form of a typical modern Closed-Circuit Rebreather (CCR) 100.

FIG. 1 shows in schematic mode of an exemplifying breathing apparatus 100 in the form of a typical modern CCR architecture, e.g. as elaborated in the patent document U.S. Pat. No. 4,964,404 (Stone). The general operation of such a CCR is as follows: the user breathes into a mouthpiece 1 that contains checkvalves (not shown) that enforce the flow of gas in a preferential direction, as schematically indicated by the arrows 29' in FIG. 1. The expelled gas (from exhalation) travels down breathing hose 2 and into junction block 3, which permits passage of the gas into a flexible bladder 4 known as a "counterlung". In advanced CCR designs (e.g. as in the patent document by Stone cited above) two counterlungs are used—an exhalation counterlung 4 and an inhalation counterlung 11 such that each has a volume equal to about half the exhalation volume of the diver. As the exhalation counterlung 4 fills the gas then continues through junction block 3 and through breathing hose 5, which carries the gas to a hose junction 275 with a gas processing unit 6. Inside the gas processing unit 6 the gas is passed through a carbon dioxide removal means 7, which frequently takes the form of an absorbent that chemically reacts with the gaseous carbon dioxide to form a carbonate molecule. The clean gas then continues on to an Oxygen Control Module 8', which i.a. performs the critical oxygen sensing and control functions of the CCR, which preferably includes at least the following tasks:

Sense the PO2 of the breathing gas

Determine whether the measured PO2 is below acceptable limits

Control a valve so as to add oxygen if the PO2 is too low

Send a signal to a display that displays the current PO2

When oxygen is added pure oxygen contained in a pressure vessel 20 with manual tank valve 21 and first stage regulator 22 sends pure oxygen gas at reduced pressure (generally at 8 to 12 bar pressure) through tube/hose means 19 to an electronically controlled valve 23 (e.g. a solenoid valve), which is connected to the Oxygen Control Module 8' by an electrical control cable 24.

There are many variations on the well known general concept as indicated above and the decision making process can be either performed using analogue or digital electronics, although the later has almost entire supplanted the former in the last decade. It is common now to have cable 25 (or wireless data relay means) leading from the Oxygen Control Module 8' to a display 26 that can provide sophisticated amounts of alphanumeric and symbolic information to the user relating to the status of the apparatus breathing apparatus 100 and, as well, tactical information both direct (e.g. present depth, tank supply gas pressures) as well as derived (e.g. decompression status, maximum depth etc) information.

The breathing gas then exits the Gas Processing Unit 6 and the Oxygen Control Module 8' at manifold 276, travels through hose 9 to junction block 10 and enters the inhalation counterlung 11, which continues to fill up until the volume of gas in counterlung 11 combined with that in counterlung 4 comprise the complete volume of gas exhaled by the user (assuming no loss). Upon inhalation, the diver first draws air (through mouthpiece 1) from the inhalation counterlung 11 until it collapses, whereupon gas remaining in exhalation counterlung 4 is pulled through the Gas Processing Unit 6 and the Oxygen Control Module 8' as described previously until the diver's lungs are full. If a diver is descending during this cycle of breathing the volume of gas in the system is reduced due to hydrostatic compression and the amount of gas inhaled by the user will be less than is required to achieve full lung volume. At this point exhalation counterlung 4 collapses and activates a diluent gas addition valve 13, which automatically provides sufficient gas to allow the user to complete inhalation where upon it ceases to add diluent gas to the system. The diluent gas which is supplied to valve 13 is provided by a pressure vessel 16 containing a supply of a breathable diluent gas. The pressure vessel contains a shutoff valve 17 and a first stage regulator 18 which reduces the pressure to between 8 to 12 bar typically and supplies this gas via tube 15 to the counterlung "Automatic Diluent Valve" or "ADV" 13 which acts as described above. When a user is ascending from depth, the reverse occurs and the user's exhaled lung volume will eventually exceed the combined volumes of counterlungs 4 and 11 and the rise in system pressure will trigger a pressure relief valve 14 that dumps the excess gas overboard. The user may then be free to initiate the next breath.

As is well known to those skilled in the art, there are many variations on the general concept of the CCR architecture 100 and similar breathing apparatus as indicated above, However, the above comprises typical basics features of modern digitally-controlled CCR apparatus and similar breathing apparatus for which the subsequent discussion herein pertain.

Basic Breathing Apparatus—Oxygen Control Arrangement

Figure 2:
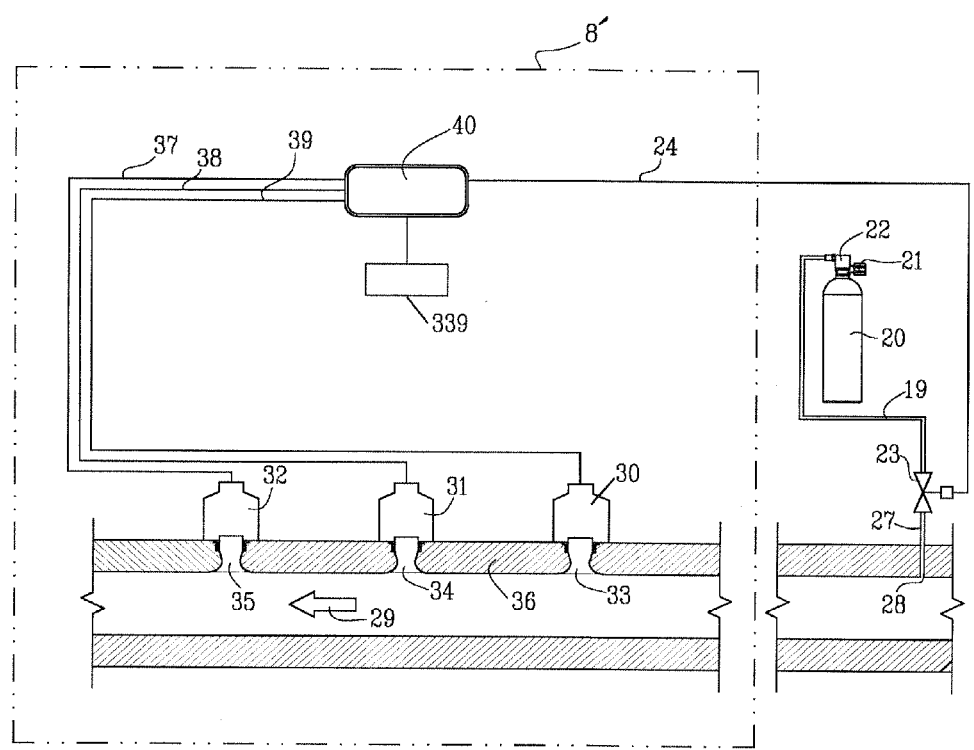
FIG. 2 shows in schematic mode an exemplifying architecture of the Oxygen Control Module 8' of the CCR in FIG. 1.

We now specifically turn our attention to what is inside the Oxygen Control Module 8' of a typical modern CCR as indicated in FIG. 1. For this purpose FIG. 2 provides a schematic architecture that shows a basic internal system including three oxygen sensors 30, 31, and 32 that attach to sensing manifold structure 36 and are exposed to the breathing gas that flows through gas pathway 29 at access ports 33, 34, and 35 respectively. The electrical signals from oxygen sensors 30, 31, and 32 are carried by electrical cables 39, 38, and 37 respectively to a control arrangement preferably a control unit 40 comprising software and/or hardware designed to process and interpret the signals and to provide that information to the decision making software and/or hardware that resides on the control unit 40. The control unit 40 is powered by one or more power means 339 such as a battery or similar that provides portable electrical power to the control unit 40. The control unit 40 can then operate oxygen solenoid valve 23 as needed via cable 24 and provide information to a display 26 via cable 25. The oxygen supply 20 and oxygen solenoid valve 23 are as previously defined in FIG. 1 with the exception that we further clarify that the output from solenoid valve 23 is sent through tube 27, which connects to manifold structure 36 and then is injected into the breathing loop at orifice 28. It is typical in all present-day CCR designs to inject the metabolic makeup oxygen at a point such that:

1) it will not cause the user at any point to directly inhale a slug of pure oxygen, and
2) it will not inject a slug of oxygen directly or near the oxygen sensors because of the risk of temporarily spoofing (confusing) the sensors.

As mentioned above in the section "Background", examples of breathing apparatuses as the one shown in FIG. 2 utilizing three oxygen sensors per se are e.g. disclosed in the patent documents U.S. Pat. No. 6,712,071 (Parker), GB 2404593 (Deas) and CA 2564999 (Straw).

The compromise that is generally reached is to inject metabolic makeup oxygen at the inlet (upstream) manifold for the carbon dioxide removal canister 7 e.g. near or at the hose junction 275 as shown in FIG. 1, such that the oxygen has a chance to mix with the gas flow prior to reaching the oxygen sensors so as to eliminate PO2 spiking of the oxygen sensors. Thus in FIG. 2 the metabolic oxygen injector orifice 28 is shown as being well upstream of the oxygen sensors 30, 31 and 32 with the flow in breathing gas pathway 29 from right to left.

Hence, prior to the disclosure of the present invention the concept of injecting oxygen even in the close proximity of the oxygen sensors would have been considered a bad idea due to the risk of temporarily affecting the oxygen sensors in a negative manner. In fact, the idea of injecting oxygen substantially directly into the oxygen sensor as in the present invention would have been, and will probably be, considered radically incorrect by mainstream CCR designers. Hence, the invention offers a non-obvious path forward to a more reliable, and safe CCR Oxygen Control System.

Additionally, in FIG. 2 all of the oxygen sensor failure scenarios described earlier in the section "Background" are extant and there is no remedy for dealing with these problems during a dive other than to read the displayed sensor values and attempt to make an immediate decision—rightly or wrongly—by human intuition alone whether they represent a life-threatening situation. It is primarily for this reason that electronically controlled CCR systems have been viewed by some as "more dangerous" than open-circuit breathing apparatuses and similar. Below follows a discussion of embodiments of the invention that will eliminate or at least mitigate the ambiguity in this crucial decision making process.

Oxygen Sensor Arrangement—Two Sensors, One Auto-Calibrated/Auto-Validated

Figure 3A:
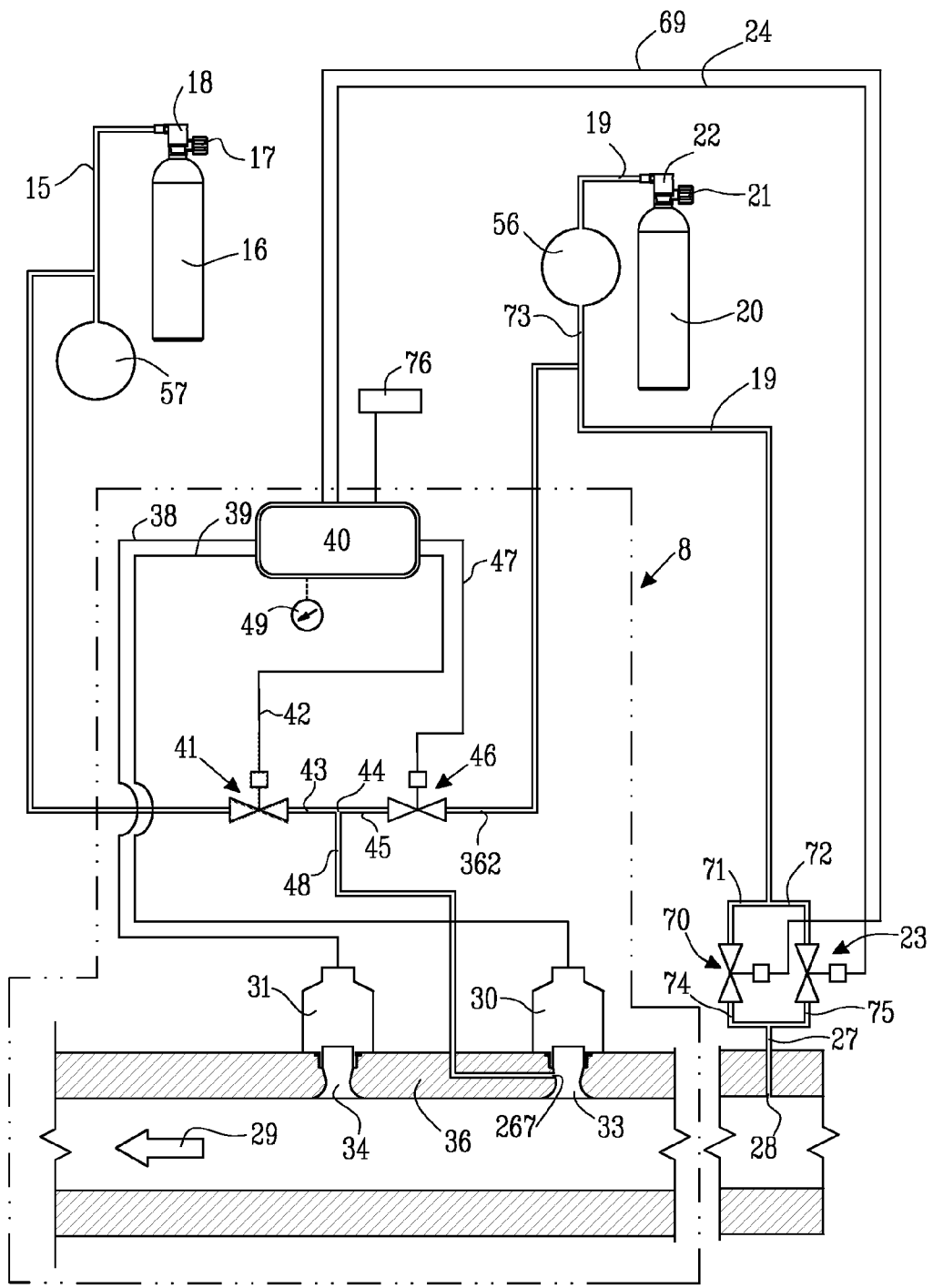
FIG. 3a shows in schematic mode an exemplifying architecture of an Oxygen Sensor Arrangement 8 for a simple embodiment of the invention comprising a Primary Oxygen Sensor and a Secondary Oxygen Sensor.

FIG. 3a shows the schematic architecture for a simple embodiment of the invention, focusing on the Oxygen Sensor Arrangement 8, corresponding to Oxygen Control Module 8' in FIG. 1.

Before we proceed it should be emphasised that he same or similar references in the Figures of the appended drawings correspond to the same or similar features, unless otherwise indicated herein. For example, the oxygen supply 20 is the same in FIGS. 1, 2 and 3a.

As can be seen in FIG. 3a, the Oxygen Sensor Arrangement 8 comprises or is at least connected to a control unit 40 according to an embodiment of the present invention. The control unit 40 is arranged to operatively control and supervise the operation of the Oxygen Sensor Arrangement 8 and the oxygen sensors in particular and the oxygen in the breathing gas in the breathing loop of the CCR 100 in general as indicated by 29' in FIG. 1, i.e. particularly the oxygen in the breathing pathway 29 in FIG. 3a that forms a part of the breathing loop 29' of the CCR 100. The control unit 40 may be implemented by means of hardware and/or software, and it may comprise one or several hardware units and/or software modules, e.g. one or several separate processor arrangements provided with or having access to the appropriate software and hardware required for the functions to be performed by the Oxygen Sensor Arrangement 8. Various programmable oxygen control modules such as module 40 capable of supervising the oxygen sensors in a CCR and the oxygen of the breathing gas in the breathing loop of a CCR are well known per se by those skilled in the art and they need no detailed description as such, see e.g. the patent documents U.S. Pat. No. 6,712,071 (Parker), GB 2404593 (Deas) and CA 2564999 (Straw) mentioned above.

However, the control unit 40 related to embodiments of the present invention comprises novel features that will be elaborated in the following.

The control unit 40 is powered by battery module 76 or a similar power source, which must not necessarily be a part of the Oxygen Sensor Arrangement 8. The ambient pressure is preferably measured by a pressure sensor 49 that transmits the pressure information to control unit 40 so that onboard firmware has, at all times and in real-time, access to the absolute ambient pressure (preferably measured in bars). It should be emphasised that the pressure sensor 49 may be omitted in some embodiments of the invention. This may e.g. be the case in embodiments that are used at a substantially constant pressure, e.g. in breathing apparatuses intended to be used at the surface, e.g. such as medical equipment (e.g. medical ventilators and respirators etc). Primary Oxygen Sensor 30 and Secondary oxygen sensor 31 are connected to the control unit 40 by signal wires 39 and 38, respectively and convey real-time information on the PO2 sensed by each sensor via access ports 33 and 34, respectively in manifold structure 36 such that each sensor is exposed to the breathing gas flow through gas pathway 29.

Control unit 40 in turn separately controls four or more microvalves 23, 70, 46, and 41 via electrical connections 24, 69, 47, and 42 respectively. Oxygen is supplied by pressure vessel 20 which includes a manual shutoff valve 21, first stage regulator 22 and a low pressure (8 to 12 bar) delivery tube 19 that connects to a low pressure accumulator volume 56. From the accumulator volume 56, tubes 73, 19, 71, and 72 transport oxygen to the metabolic makeup microvalves 23 and 70 which are both of a normally-closed design. It is preferred that when the control unit 40 determines that the measured PO2 (following calibration and validation, which we will discuss below) is below the PO2 control setpoint by some pre-set tolerance, tol, (e.g. determined by means of empiric test) a signal is sent to open the primary metabolic oxygen makeup solenoid microvalve 23 such that oxygen is sent through tubes 75 and 27 to the injection port 28 into the gas processing unit 6, see FIG. 1. It is preferred that the injection point 28 is arranged upstream of the carbon dioxide canister 7 and downstream of the breathing hose 5, such that the injected oxygen will be mixed with the breathing gas as it passes through the carbon dioxide absorbent chamber 7 prior to reaching the oxygen sensors 30, 31. As can be seen in FIG. 3a it is further preferred to have a second parallel, normally un-used metabolic makeup oxygen injection microvalve 70 that can be activated when the control unit 40 determines that more metabolic makeup oxygen is needed than is capable of being supplied solely by the primary oxygen microvalve 23 or in the event of a failure in the closed state of microvalve 23.

The oxygen test microvalve 46 connected to oxygen tubes 73 19 via tube 362 is primarily dedicated to automated calibration of the Primary Oxygen Sensor 30. The output of microvalve 46 travels through tube 45 to junction 44, and then via tube 48 to a test orifice 267 from which the output is injected to the access port 33 of the oxygen sensor 30.

It is preferred that the test orifice 267 or similar opening is arranged in a position that is adjacent to or directly adjacent to the Primary Oxygen Sensor 30 so that the distance between the test orifice 267 and the oxygen sensor 30 (preferably the sensing surface of the oxygen sensor or similar part of the oxygen sensor preferably arranged in the access port 33) is less than 150 millimeters (mm), or less than 100 millimeters, or less than 50 millimeters, or less than 25 millimeters, or less than 20 millimeters, or less than 15 millimeters, or less than 10 millimeters, or less than 5 millimeters, or less than 2.5 millimeters, or less than 1 millimeter or less than 0.5 millimeter, but preferably larger than 0.1 millimeter.

It is also preferred that the gas from the test orifice 267 is injected into the access port 33 of the oxygen sensor 30 in such a fashion as to create turbulence that will lift condensation off of the sensing surface of sensor 30 but not cause damage to that surface. At the same time, the surface will thus be exposed to a burst of pure oxygen with a PO2 corresponding to pure oxygen at the ambient pressure sensed by pressure sensor 49.

It is also preferred that the access port 33 of the Primary Oxygen Sensor 30 is implemented as a cavity in the sensing manifold structure 36 enclosing the gas pathway 29 so as to define a test volume that is preferably smaller than 100 milliliters (mL), or smaller than 90 milliliters, or smaller than 80 milliliters, or smaller than 70 milliliters, or smaller than 60 milliliters, or smaller than 40 milliliters, or smaller than 30 milliliters, or smaller than 20 milliliters, or smaller than 10 milliliters or smaller than 5 milliliters, but preferably larger than 1 milliliter, or larger than 2 or larger than 3 milliliters. Consequently it is preferred that the test valves 41, 46 are controlled by the control unit 40 so as to provide an amount of gas to the Primary Oxygen Sensor 30 that corresponds to the volume of the cavity of the access port 33 for the Primary Oxygen Sensor 30, e.g. provide a volume that is substantially equal to or less than the volume of the cavity or twice that volume and hence preferably at least not larger than 200 milliliters.

In a similar manner as the oxygen gas described above, diluent gas is provided to the test orifice 267 and the access port 33 via pressure vessel 16 which includes a manual shut-off valve 17, first stage regulator 18 and a low pressure (8 to 12 bar) delivery tube 15 that connects to a low pressure accumulator volume 57. The purpose of accumulator 57 is to provide a significant volume of low pressure gas adjacent or immediately adjacent the associated diluent test microvalve 41 such that when that valve is commanded to add gas that line pressure loss effects do not prevent the required volume from being injected through the valve 41. From the accumulator 57, tube 15 continues to the diluent test microvalve 41 which is of a normally-closed design. The output of microvalve 41 proceeds through delivery tube 43 to junction 44. From there it proceeds through tube 48 and is injected into the cavity 33 of the Primary Oxygen Sensor 30 at orifice 267, i.e. the same as for the oxygen gas injection described above.

It is also preferred that the control arrangement 40 comprises information or is arranged to operatively receive information corresponding to the fraction of oxygen in the diluent (e.g. air with approximately 21% oxygen) and/or in the oxygen (approximately 100% oxygen), so as to be able to operatively compare said representation with measures from the Primary Oxygen Sensor 30 obtained when the sensor 30 is provided with an amount of gas via the test orifice 267 by means of test valves 41 and/or 46. For example, the control arrangement 40 may be provided with information about the fraction of oxygen in the diluent and/or oxygen in question by the user actuating buttons or similar input means on the Oxygen Sensor Arrangement 8 or on the display unit 26 or similar before a dive. Alternatively, information corresponding to the fraction of oxygen in the diluent and/or oxygen to be used may be provided to the control unit 40 during manufacturing or distribution or similar, or it may be provided by information read from the diluent source and/or oxygen source 20 when these sources are connected to the CCR 100 and the control unit 40, e.g. read by means of electric signals communicating with a memory or similar comprised by the source 16, 20.

Given the exemplifying architecture as outlined above, the oxygen auto-calibration and/or testing method according to embodiments of the invention provide a series of particularly advantageous capabilities as will be further elaborated below.
True Automated Pre-Dive Calibration Referring again to FIG. 3a, at initial power-up at the surface before use of the CCR 100 according to an embodiment of the present invention, control unit 40 will automatically fire the diluent test microvalve 41 to inject a burst of pure diluent gas (e.g., air) substantially directly on the Primary Oxygen Sensor 30, reliably exposing it to a known low-oxygen mixture at the ambient pressure. The output signal from oxygen sensor 30 is then stored by the control unit 40 (preferably in a non-volatile memory) as a first oxygen calibration point. Next, control unit 40 will automatically fire the oxygen test microvalve 46 to inject a burst of pure oxygen directly on the Primary Oxygen Sensor 30, reliably exposing it to pure oxygen at the ambient pressure. The output signal from sensor 30 is then stored by the control unit 40 (preferably in a non-volatile memory) as a second oxygen calibration point. In actual practice, it is preferred that a plurality of readings (e.g. at least 10 readings) are made at each calibration point and the results averaged. In both cases (diluent and oxygen injection) the ambient pressure is preferably measured via pressure sensor 49. The ambient pressure (absolute), combined with the known decimal fractional content of oxygen (FO2) in both the diluent (at 1 bar at the surface, air, for example, would have an FO2 of 0.21) and the pure oxygen supply (FO2=1.0), allows for the direct calculation of the PO2 at the two calibration points from which a linear or at least substantially linear calibration curve (see FIG. 5 and or 7) can be automatically generated and stored by the control unit 40 (preferably in a non-volatile memory). It is preferred that this stored curve that will be used throughout a dive for the determination of metabolic oxygen makeup gas injection, unless one of the trigger events listed below occurs first.

Figure 3B:
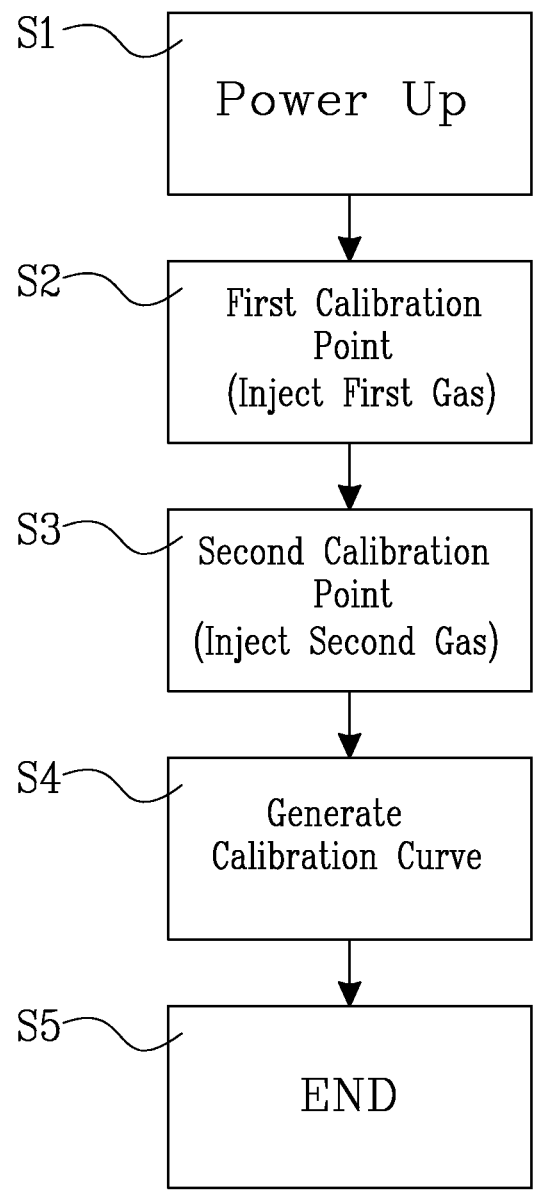
FIG. 3b shows an exemplifying pre-dive calibration according to an embodiment of the present invention.

FIG. 3b shows an exemplifying pre-dive calibration according to an embodiment of the present invention as indicated above.

In a first step S1 it is preferred that the CCR 100 and the control unit 40 are powered up. This step may e.g. include diagnostic activities and other start up routines.

In a second step S2, the system will start a calibration of the Primary Oxygen Sensor 30 by automatically injecting a burst of pure diluent gas (e.g., air) substantially directly on the Primary Oxygen Sensor 30, reliably exposing it to a known low-oxygen mixture. This is accomplished by the control unit 40 actuating the diluent test valve 41 in FIG. 3a. Here, it is also preferably that the ambient pressure is measured by the pressure sensor 49.

This is preferably done just before or during the injection of diluent gas. It is preferred that the output signal from the oxygen sensor 30 and the pressure sensor 49 or representations thereof are stored by the control unit 40 as a first oxygen calibration point.

In a third step S3, the system will automatically inject a burst of pure oxygen gas substantially directly on the Primary Oxygen Sensor 30, reliably exposing it to pure oxygen. This is accomplished by the control unit 40 actuating the oxygen test valve 46 in FIG. 3a. Optionally the ambient pressure may be measured again by the pressure sensor 49, just before or during the injection of oxygen gas. It is preferred that the output signal from the oxygen sensor 30 and the pressure sensor 49 or representations thereof are stored by the control unit 40 as a second oxygen calibration point.

Figure 5:
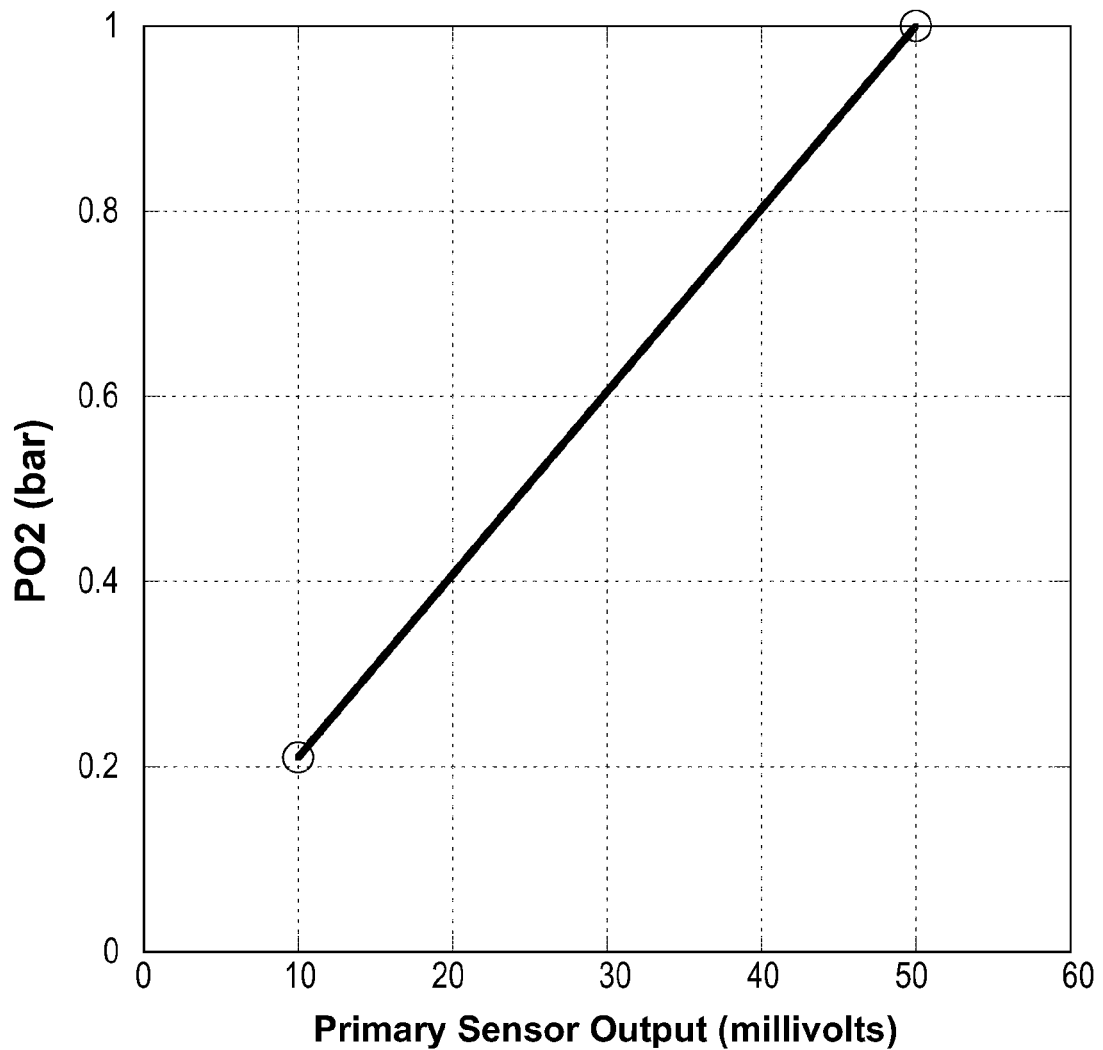
FIG. 5 shows an exemplifying substantially linear 2-point calibration curve.
Figure 6:
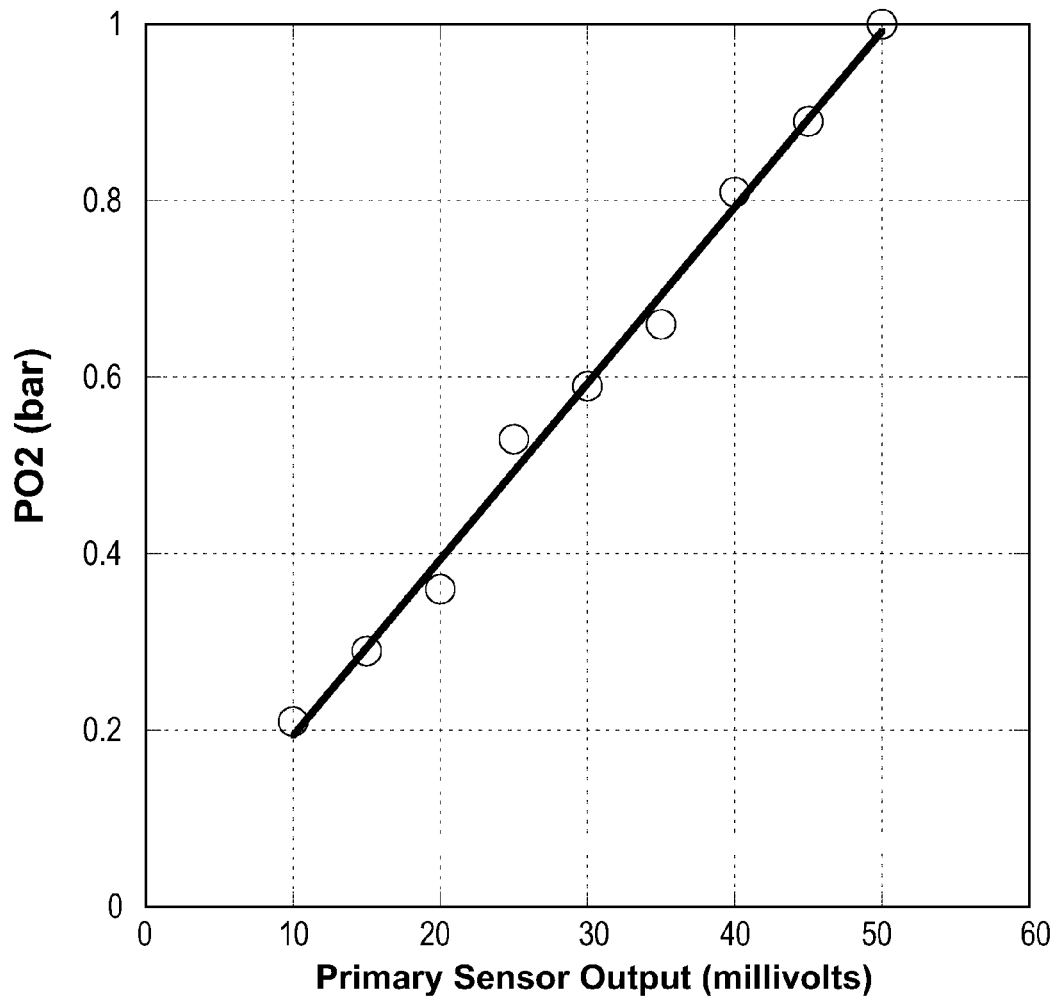
FIG. 6 shows an exemplifying number of validation points.

In a fourth step S4 it is preferred that the system (preferably the control unit 40) calculates a calibration curve based on the two oxygen calibration points obtained in step S2 and S3, see FIG. 5. This is preferably accomplished by calculating the PO2 at the two oxygen calibration points, which can be done in a well known manner by utilising the measures from the oxygen sensor 30 and the pressure sensor 49. The two oxygen calibration points are then preferably used to generate a linear or at least substantially linear calibration curve, which is preferably stored by the control unit 40.

The pre dive calibration ends in a fifth step S5. The fifth step S5 may check whether the calibration was successful or not. For example, it may be checked whether the two calibration points obtained in step S2 and S3 respectively are reasonable. For example, the first calibration point should produce a PO2 near 0,21 if air is used and the second calibration point should produce a PO2 near 1,0 if oxygen is used. If this is not the case an abortion notification may be produced by the control unit 40.

In-Dive Sensor Validation with Diluent Gas

Referring again to FIG. 3a, periodically during the course of a dive (possibly more often than every 30 second, or more often than every minute, or more often than every two minutes, or more often than every three minutes, or more often than every four minutes, or more often than every five minutes, but generally on a 5 to 10 minute interval, although this value can be stored by the control unit 40 (preferably in a non-volatile memory) as a user-definable constant) the control unit 40 will cause diluent test microvalve 41 to fire and thus inject a small burst of diluent gas into the oxygen sensor cavity 33 via injection orifice 267. This burst of diluent gas will have the previously described primary effects of automatically removing condensate from the sensing surface of Primary Oxygen Sensor 30 and simultaneously exposing the sensing surface to a gas mixture with a fixed FO2 (decimal fraction of oxygen). The control unit 40 will then obtain the resultant PO2 reading from Primary Oxygen Sensor 30 and obtain the current ambient pressure from the pressure sensor 49. With the ambient pressure sensor 49 and a known oxygen fraction (FO2) in the diluent supply 16, the Primary Oxygen Sensor 30 can be exposed to a known partial pressure of oxygen (PO2) at any moment during the dive, and monitored to ensure that the sensor responds with the correct reading. The correct reading is simply the absolute ambient pressure (in bar) times the known FO2 of the diluent. Repeated failure of this test will cause the control unit 40 to initiate an alert to the diver that the dive should be aborted immediately. The alert can be issued by means of any safety system well known to those skilled in the art as being commonly used in CCRs, including but not limited to visual and/or audible signalling.

Figure 3C:
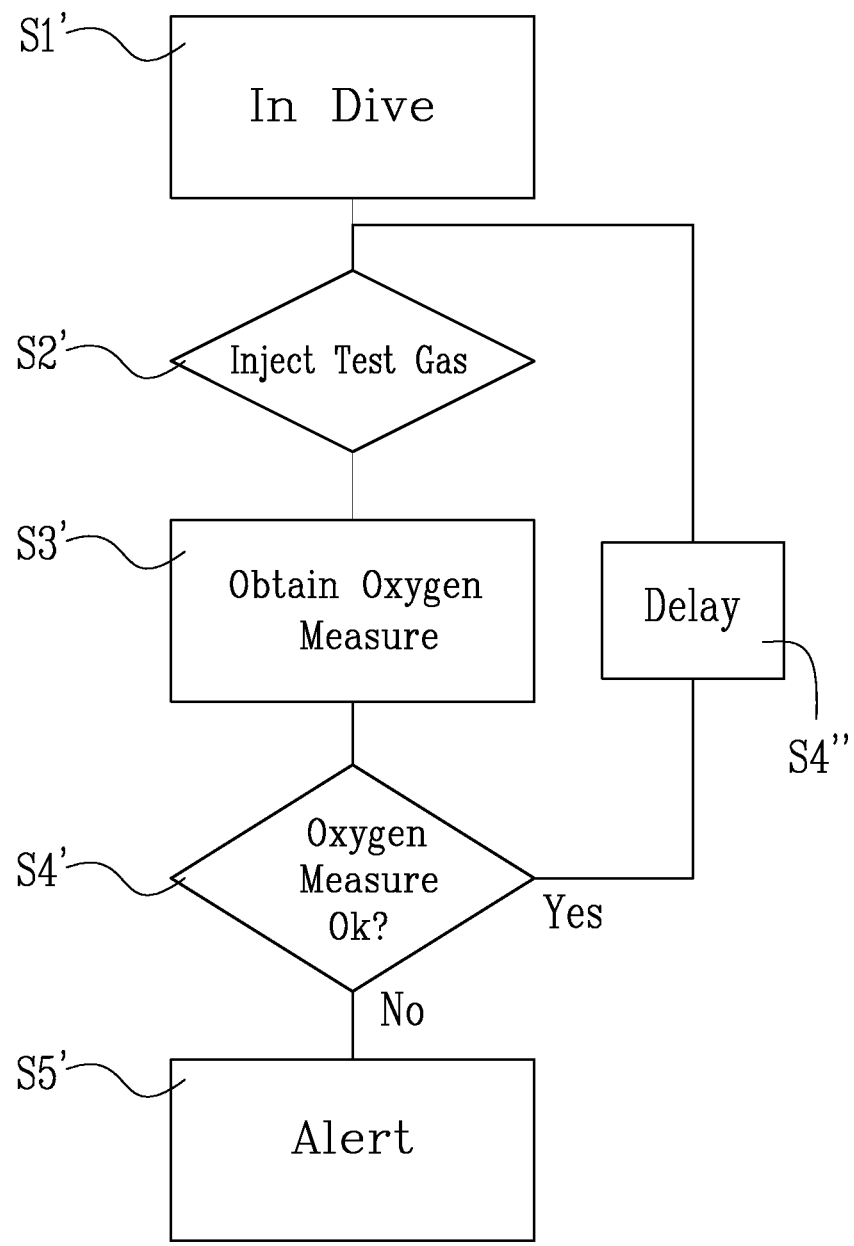
FIG. 3c shows an exemplifying in-dive validation according to an embodiment of the present invention.

FIG. 3c shows an exemplifying in-dive validation according to an embodiment of the present invention as indicated above.

In a first step S1' according to the present embodiment it is preferred that the CCR 100 and the control unit 40 are active. The CCR may e.g. be active under water or otherwise active at an ambient pressure above 1 bar. However, other embodiments of the invention may certainly be active at other pressures, e.g. embodiments of the invention implemented in breathing apparatuses that are active at the surface at an ambient pressure of substantially 1 bar.

In a second step S2', the system will start a validation of the Primary Oxygen Sensor 30 by automatically injecting a burst of pure diluent gas (e.g., air) substantially directly on the Primary Oxygen Sensor 30, reliably exposing it to a known low-oxygen mixture. This is accomplished by the control unit 40 actuating the diluent test valve 41 in FIG. 3a.

In a third step S3' during the exposure of the Primary Oxygen Sensor 30 a measure is obtained from the oxygen sensor 30 and from the pressure sensor 49. The pressure is preferably measured just before or during the injection of diluent gas. At each such occasion it is preferred that the output signal from the oxygen sensor 30 and the pressure sensor 49 or representations thereof are stored by the control unit 40 as validation points, see the circles in FIG. 8.

In a fourth step S4' it is preferred that the system (preferably the control unit 40) calculates the expected PO2 for the validation point using the known fraction of O2 in the diluent and the current ambient pressure obtained from the pressure sensor 49. The expected value for the validation point value is preferably calculated by using the calibration curve so as to compensate for possible acceptable deviations in the Primary Oxygen sensor 30. The expected PO2 is then compared to the measure obtained from the Primary Oxygen Sensor 30.

The validation process proceeds to a fifth step S5 if the difference between the expected PO2 and the measure obtained from the Primary Oxygen Sensor 30 exceeds a predetermined threshold and an alert is issued. The threshold may e.g. be determined by means of empirical investigations.

The validation process proceed to delay step 4" if the difference between the expected PO2 and the measure obtained from the Primary Oxygen Sensor 30 is at or below the predetermined threshold and the process is stayed for a predetermined time before returning to the second step S2' to inject another burst of diluent gas on the Primary Oxygen Sensor 30. The predetermined time may e.g. be determined by means of empirical investigations. For example, it may correspond to a validation interval of less than 30 second, less than a minute, less than two minutes, less than three minutes, less than four minutes, less than five minutes, but generally less than a 5 to 10 minute interval.

During the time of the automated testing procedure described above it is preferred that the control unit 40 disables firing of the metabolic oxygen microvalves 23 and 70 and continues to prevent firing after termination of the test for a period necessary to flush the access port 33 of the Primary Oxygen Sensor 30 with uniform breathing gas from the user. This duration is design specific but in general will be approximately 8 to 10 seconds following the termination of the gas pulse entering the sensing cavity 33.

Although in theory the in dive validation could be done through the use of either diluent or pure oxygen, it is safer to use diluent since it can be injected safely over the entire range of possible ambient pressure profiles without the risk of excess gas addition leading to a potential oxygen toxic state. Furthermore, most oxygen sensors have a limiting output value and this value can be easily exceeded if pure oxygen were injected, for example, during the deeper portions of a dive. For these reasons, it is recommended that most auto-validation is done with diluent gas.

A Secondary Oxygen Sensor

The Secondary Oxygen Sensor 31 and access port 34 are preferably the same or similar as the Primary Oxygen Sensor 30 and access port 33. However, the access port 34 of the Secondary Oxygen Sensor 32 shown in FIG. 3a is not provided with a test orifice such as the test orifice 267 in the access port 33. The access port 34 may therefore have a shape that differs from the shape of access port 33. The primary function of the Secondary Oxygen Sensor 31 is that of auxiliary verification of the functional state of the Primary Oxygen Sensor 30 and cross-correlation that there are no leaks in either of the test microvalves 41 and 46. The Secondary Oxygen Sensor 31 is thus an aid to making the go/no-go (abort/continue) decision that is made primarily based on the PO2 measured by the Primary Oxygen Sensor 30. Hence it is preferred that the Secondary Oxygen Sensor 31 monitors the oxygen content of the breathing gas while the Primary Oxygen Sensor 30 is being validated. It is also preferred that the Secondary Sensor 31 is used to detect possible leakage in the test valves 41 and/or 46 as described in more detail below. However, it should be mentioned that leakage detection using two primary oxygen sensors and no secondary oxygen sensor would require at least one extra test valve in addition to the test valves 41 and 46. In addition, it is possible to supply a more extensive injection of diluent via the test orifice 267 into the access port 33 of the Primary Oxygen Sensor 30 so that the injected diluent flows out of the access port 33 and into the access port 34 and the Secondary Oxygen Sensor 31. An advisory warning message or an abort message can be issued if the Secondary Oxygen Sensor 31 provides a good PO2 value while the Primary Oxygen Sensor 30 provides a bad PO2 value, or if both the Secondary Oxygen Sensor 31 and the Primary Oxygen Sensor 30 provides a bad PO2 value.

In-Dive Sensor Calibration and Validation with Oxygen

When conducting an oxygen sensor calibration at sea level standard temperature and pressure (STP) it is only possible to obtain a maximum sensor response of 1 bar PO2 from a sensor when exposed to pure oxygen. Obtaining any higher PO2 reading requires the presence of an ambient absolute pressure greater than 1 bar. However, it is also known that a very common class of chemical (fuel cell) type oxygen sensors that comprise the vast majority of all oxygen sensors used in CCR breathing apparatus are subject to degradation in performance above 1 bar PO2 with aging (see FIG. 3f). The aging degradation manifests itself as a departure from an extended calibration curve obtained as will be described below. Current CCR designs have no means of detecting such aging effects.

Figure 7:
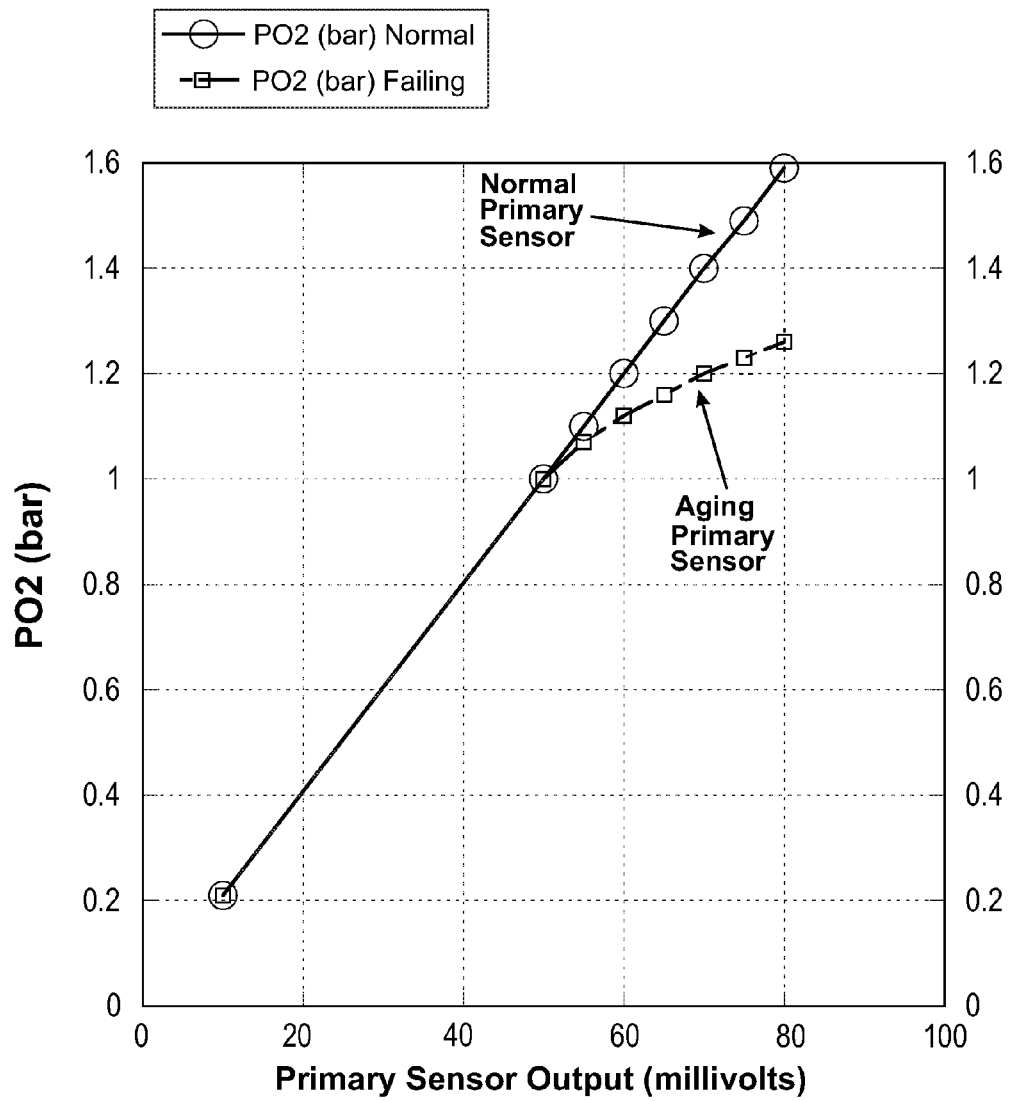
FIG. 7 shows an exemplifying substantially linear calibration curve based on 3 or more calibration points.

Referring again to FIG. 3a, during the descent on a dive (after the surface pre-dive calibration has been performed and the diver has begun a descent underwater) and at a point preferably greater than or equal to 5 meters deep (approximately 1.5 bar) but preferably not deeper than 10 meters (approximately 2.0 bar), and preferably following a successful diluent gas PO2 validation check, the control unit 40 will issue a command to fire the Oxygen Test Valve 46 and inject a small volume of pure oxygen into sensing cavity 33 via jet orifice 267. In other words, an additional calibration point is obtained by the control unit 40 actuating Test Valve 46 at least once to provide an amount of pure oxygen to the oxygen sensor 30 while the ambient pressure is in the interval of approximately 1,5 bar to 2,0 bar, preferably measured by the pressure sensor 49. Knowing the FO2 fraction is 1.0 for oxygen and knowing the ambient absolute pressure from sensor 49 the control unit 40 will preferably calculate the true PO2 and store that value (preferably in a non-volatile memory). Given the above, the control unit 40 will obtain an extended calibration curve, see FIG. 7. The extended calibration curve is preferably based on the two calibration points previously obtained during surface pressure at the pre-dive calibration and at least the third calibration point now obtained under underwater pressure during dive, e.g. obtained at substantially 1,6 bar or points obtained during a number of pressures between substantially 1 bar to substantially 1,6 bar). Preferably the curve fit is accomplished by a non-linear 3-point least squares optimized curve fit. The extended calibration curve is preferably stored by the control unit 40 (preferably in a non-volatile memory), preferably together with the new extended calibration curve coefficients (linear, parabolic, or cubic depending on the best closed-form fit). This extended range calibration and/or check need only be done one per dive and the results will be compared against previous results logged in non-volatile memory and the trends analyzed. A sensor rejection algorithm analyzes the data and determines whether the latest extended range calibration is within allowable specification. If not, the firmware will issue safety advisory warnings to the diver.

It is generally not recommended to exceed an operating PO2 of 1.6 bar in a CCR for reasons of user safety and avoidance of oxygen toxicity effects. Thus the procedure just described would be executed only briefly at one or a few key points between the absolute ambient pressure of 1.0 to 1.6 bar (approximately sea level on the surface to about 6 meters depth underwater). If we were to acquire such points at $\frac{1}{10}^{th}$ bar increments in absolute ambient pressure during a diving descent from the surface to 6 meters depth, we might obtain the data represented by the circles in FIG. 3f for a properly functioning, new oxygen sensor. If the sensor was old, we might see the type of data represented by the square data points in FIG. 3f.

During the time of the automated testing procedure described above it is preferred that the control unit 40 disables firing of the metabolic oxygen microvalves 23 and 70. It is even more preferred that the control unit 40 continues to prevent firing after termination of a dive test for a period necessary to flush the primary oxygen sensing cavity 33 with uniform breathing gas from the user. This duration is design specific but in general will be approximately 8 to 10 seconds following the termination of the calibration gas pulse entering the sensing cavity.

Three Sensor System, Two Auto-Calibrated/Auto-Validated Sensors

The architecture described above with reference to FIG. 3a is specifically tailored to a "sport" class CCR in which the certainty of detection of the true PO2 is very high because of the just-described ability to auto-calibrate the system (both on the surface and, as well, to extend the calibration curve to high PO2 zones not reachable on the surface) and to auto-verify the PO2 during the course of a dive. However, a system using the control architecture shown in FIG. 3a is not truly redundant and a failure of the single Primary Oxygen Sensor 30 to deliver the anticipated value during a dive is grounds for an abort to the surface, preferably using an alternate life support system. Typically this is provided by the diver carrying a secondary open circuit "bailout" system that will get them to the surface, and it is assumed that a direct abort-to-surface ascent is possible—that is, technical diving inside sunken ships, inside caves, or any diving involving required decompression should preferably not be a part of the dive plan. While FIG. 3a shows a Secondary Oxygen Sensor 31 this secondary sensor does not constitute a truly redundant backup PO2 measurement system. The role of the secondary sensor 32, as stated earlier, is that of auxiliary verification of the functional state of the Primary Oxygen Sensor and cross-correlation that there are no leaks in either of the auto-calibration microvalves. The secondary oxygen sensor 31 is thus an aid to making the go/no-go (abort/continue) decision that is made primarily based on the PO2 measured by the Primary Oxygen Sensor 30. For the purposes of purely recreational CCR diving (defined as having a direct abort-to-surface ability at any time during a dive) this architecture is compact, safe, and adequate for the purpose.

Figure 4:
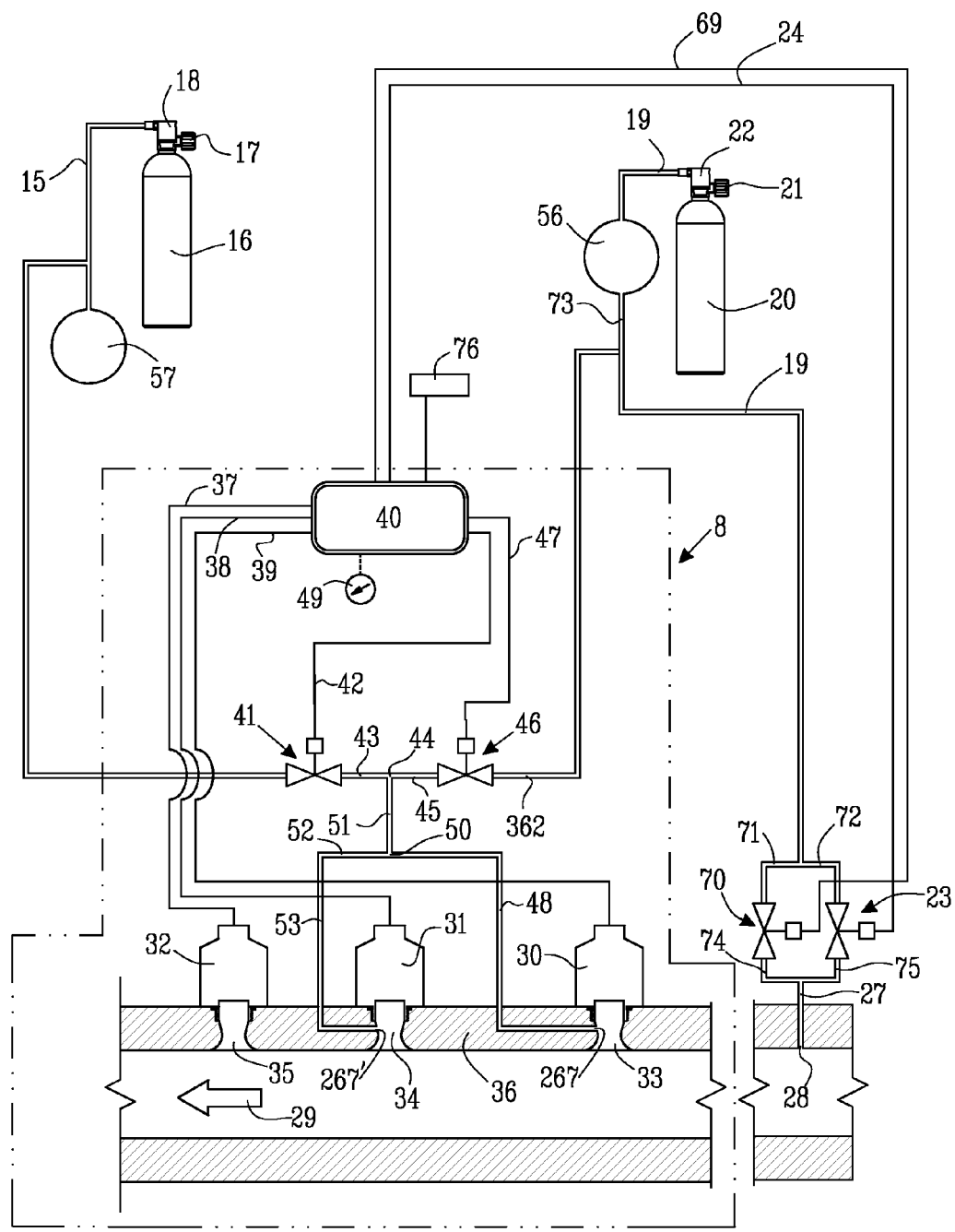
FIG. 4 shows a design that is substantially identical to the one described in FIG. 3a but with three sensors—two auto-calibrated.

FIG. 4 shows a CCR design that is substantially identical to the one described in FIG. 3a, but with the following changes:
- a third oxygen sensor 32 mounted on manifold structure 36 with access port 35 to the breathing loop 29 has been added. The Third Oxygen Sensor 32 and access port 35 are the same or similar as the Primary Oxygen Sensor 30 and access port 33 previously discussed with reference to FIG. 3a. Sensor 32 is electrically connected to the control unit 40 via electrical cable 37. Sensor 32 is not subjected to an active calibration and/or validation and it assumes the role of the "Secondary" oxygen sensor.
- Oxygen sensor 31, being connected to the control unit 40, is now treated by the control unit 40 as a redundant (parallel) Primary oxygen sensor being identical or substantially identical to sensor 30 in function and form.
- The gas outputs from the Diluent Test Valve 41 and Oxygen Test Valve 46 that join at junction 44 as previously described now travel through tube 51 to junction 50 whereupon tube 48, as previously in FIG. 3a, conducts diluent and oxygen to sensor 30. In addition, now, tube 52 and 53 conducts diluent and oxygen to sensor 31 from junction 50 to a test orifice 267' being the same or similar as test orifice 267 for sensor 30.

In this design both auto-calibrated and/or auto-validated oxygen sensors 30 and 31 are fed by the same gas distribution pathways ("tubes" 43, 45, 51) from the separate gas sources 16 and 20, respectively diluent and oxygen. A persistent leak in either the diluent test microvalve 41 or the oxygen test microvalve 46 will spoof (confuse) the readings on both sensors 30 and 31. However, sensor 32, because it is not connected to any of the gas sources 16 or 20, serves to detect such leaks through analysis by the control unit 40 of the data streams from the sensors 30, 31, 32. In the absence of an open-state failure in the normally-closed microvalves 41 and 46 both sensors 30 and 31 are subject to both the auto-calibration and auto-validation procedures described above and as such, the firmware operating on control unit 40 could directly detect that one of either sensors 30 or 31 did not pass a particular test but that the other did. If this situation occurred during the course of a dive then the onboard PO2 control system would cease to use both sensors 30 and 31 for the basis of PO2 control and revert to using the one that passed the particular test. Note, however, that because sensors 30 and 31 are not independently isolated from the potential failure of microvalves 41 or 46, the design of FIG. 4 is not precisely a duplex redundant design. It is, however, clearly more survivable than the design of FIG. 3a because it can solve the common problem of asymmetric condensate formation on oxygen sensors and validate the operational sensors, of which there are now two chances for delivering validated data instead of one.

Auto Calibration/Validation of Secondary Sensor

In FIGS. 3a and 4 we described simple auto-calibration/auto-validation system for a breathing apparatus in which at least one oxygen sensor is configured for direct auto-calibration/auto-validation by the methods previously described and this sensor is designated the "primary" oxygen sensor. In these same figures at least one oxygen sensor is not connected to the auto-calibration/auto-validation system and it is referred to as the "secondary" oxygen sensor, whose purpose and benefits have been described previously.

The question now arises, how does one calibrate the secondary sensor(s)? In the text and figures below we describe an embodiment of a new method for auto-calibrating/auto-validation the secondary sensor. The method does not rely on crude principles such as the prior art manual calibration procedures, nor does it requires special test valves other than the ones assigned to the primary sensor. The new method described here forms the basis for a continuous auto-calibration/auto-validation process that improves and enhances the secondary sensor calibration validation with every use of the breathing apparatus.

During the course of a mission (e.g. an underwater dive) and in particular during either a descent or ascent underwater in which the absolute ambient pressure is either increasing beyond 1.0 bar or decreasing from some higher absolute ambient pressure towards 1.0 bar) both the primary and secondary oxygen sensors are simultaneously exposed to a variety of absolute ambient pressures (e.g. from 1 bar to as high as 5 or 6 bar during normal sport diving activities). Similarly, both sensors are simultaneously exposed to the same breathing gas flow through the CCR.

If during a dive, the primary oxygen sensor fails an in-water validation (described above), then it may be necessary to switch control to a secondary oxygen sensor. As already indicated, this then raises the question of how to:

1. Calibrate the secondary sensor(s)
2. Validate the secondary sensor(s) during the dive.

There is elegance in simplicity and compactness and the objective of this section is to present a method of obtaining the benefits of auto-calibration/auto-validation for systems in which there are a plurality of oxygen sensors but not all of them have access to direct auto-calibration/auto-validation, i.e. some oxygen sensors are secondary oxygen sensors.

Figure 3D:
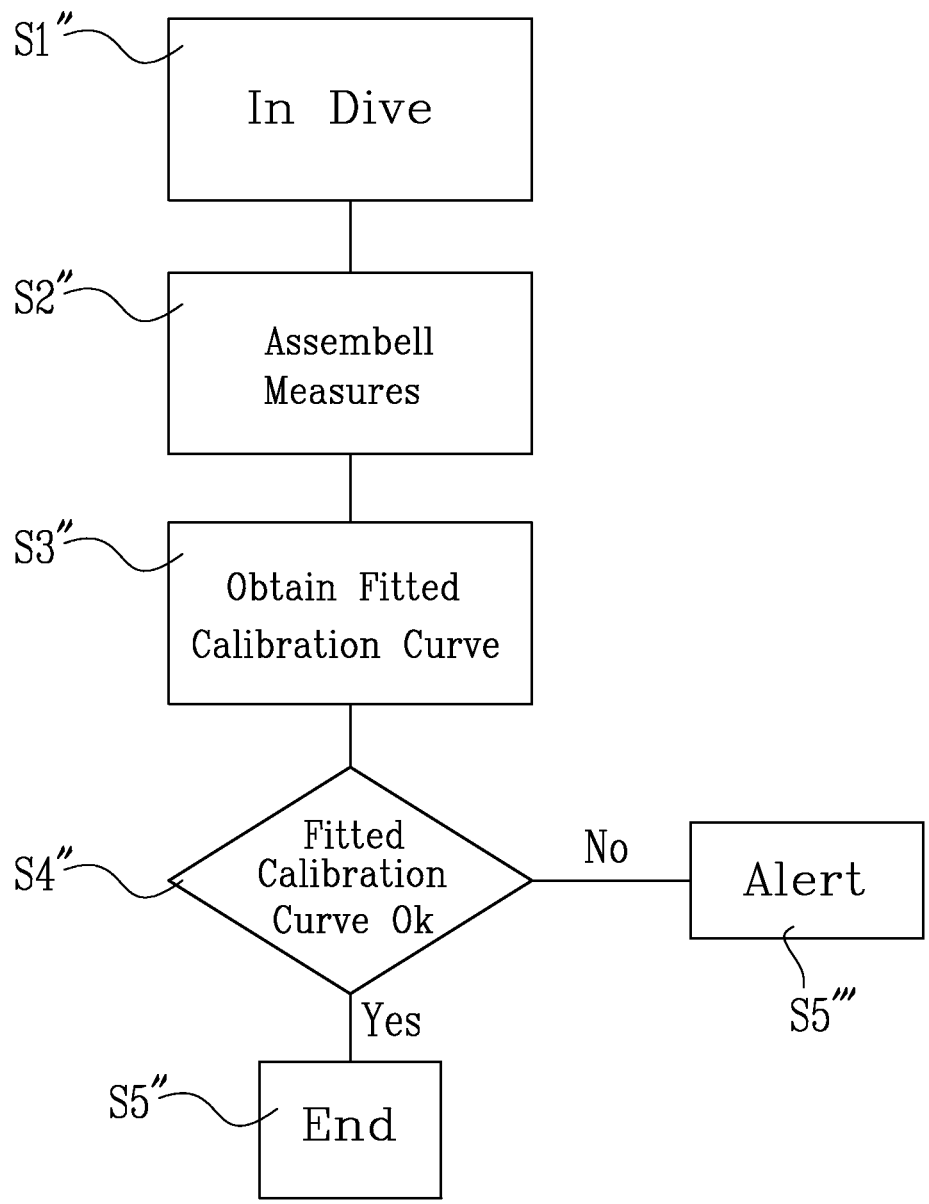
FIG. 3d shows an exemplifying transfer calibration according to an embodiment of the present invention.

FIG. 3d shows an exemplifying method according to an embodiment of the present invention for auto calibrating a secondary oxygen sensor. The method is described below with reference to the Oxygen Sensor Arrangement 8 in FIG. 3 having one primary oxygen sensor 30 and one secondary oxygen sensor 31. However, it should be emphasised that the method applies to other embodiment of the invention having at least one primary oxygen sensor and at least one secondary oxygen sensor.

In a first step S1" of the exemplifying method illustrated in FIG. 3d it is preferred that the CCR 100 and the control unit 40 are powered up. This step may e.g. include diagnostic activities and other start up routines. It is also preferably that the primary oxygen sensor 30 is calibrated as described above. For the secondary oxygen sensor 31 it is preferably the last known calibration curve is used. In a virgin system, this may involve the sensor 31 using a default calibration curve. A typical default calibration curve for a primary oxygen sensor is shown in FIG. 5.

In a second step S2" of the exemplifying method illustrated in FIG. 3d it is preferred that the diver descends in closed circuit mode at the start of a dive. The PO2 in the breathing loop 29 will then typically increase from 0.21 to a value around 1.2 bar. During the descent, the control unit 40 records a table of readings from at least one primary sensor 30 and one secondary sensor 31.

Preferably, all valid PO2 data are assembled, preferably for at least one primary oxygen sensor 30 and at least one secondary oxygen sensors 31 are assembled. Preferably this includes the auto-calibration curve for the primary sensor 30, the auto-validation and extension data for the primary sensor 30, and all other simultaneously acquired data for the secondary sensors 31 at substantially identical absolute ambient pressures and times as the values recorded for the primary sensor 30. Excluded from this data are preferably the secondary sensor readings at the times of auto-calibration, auto-validation, and auto-extension for the primary sensor and for the breathing gas re-mix periods following those events (approximately 15 seconds in general). It is preferred that the readings from the oxygen sensors 30, 31 are matched time-stamp pairs. These data are then organized (by storage array with each entry for the primary and secondary sensors having matched time stamps) into the form of a function:

$Y=f(x)$

Where: X=the array of secondary oxygen sensor PO2 values
Y=the array of primary oxygen sensor PO2 values For a 2-sensor CCR this data might look like that presented in FIG. 8, with the circles representing the measured response of the primary sensor 30 and the triangles representing the response of the secondary sensor 31.

Figure 8:
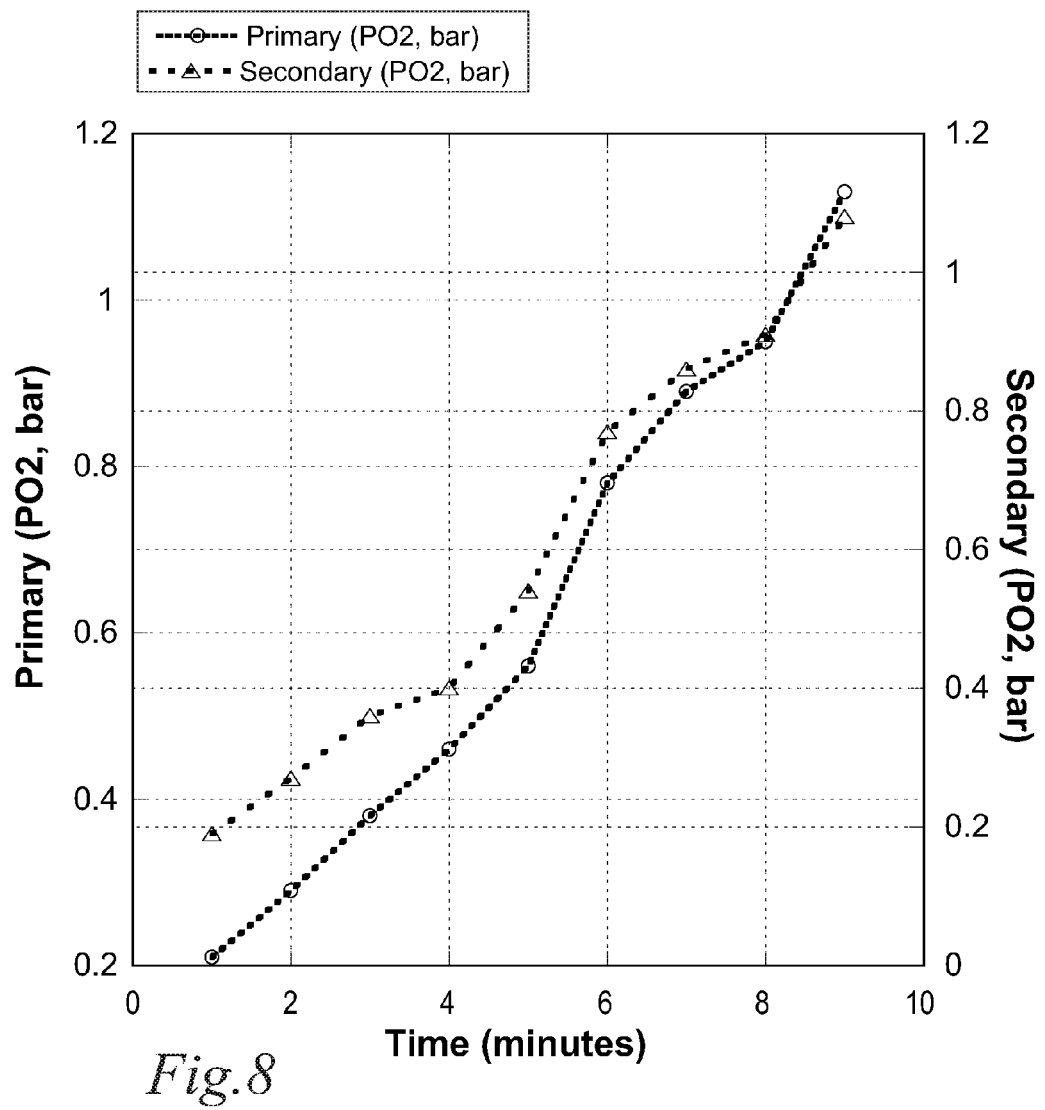
FIG. 8 is a schematic illustration of simplistic exemplifying readings obtained from primary and secondary oxygen sensors during a descent.

The data shown in FIG. 8 are simplistic. The method now described, however, is valid across substantially all possible closed-cycle breathing apparatus mission profiles. This applies mutatis mutandis for other breathing apparatuses.

Figure 10:
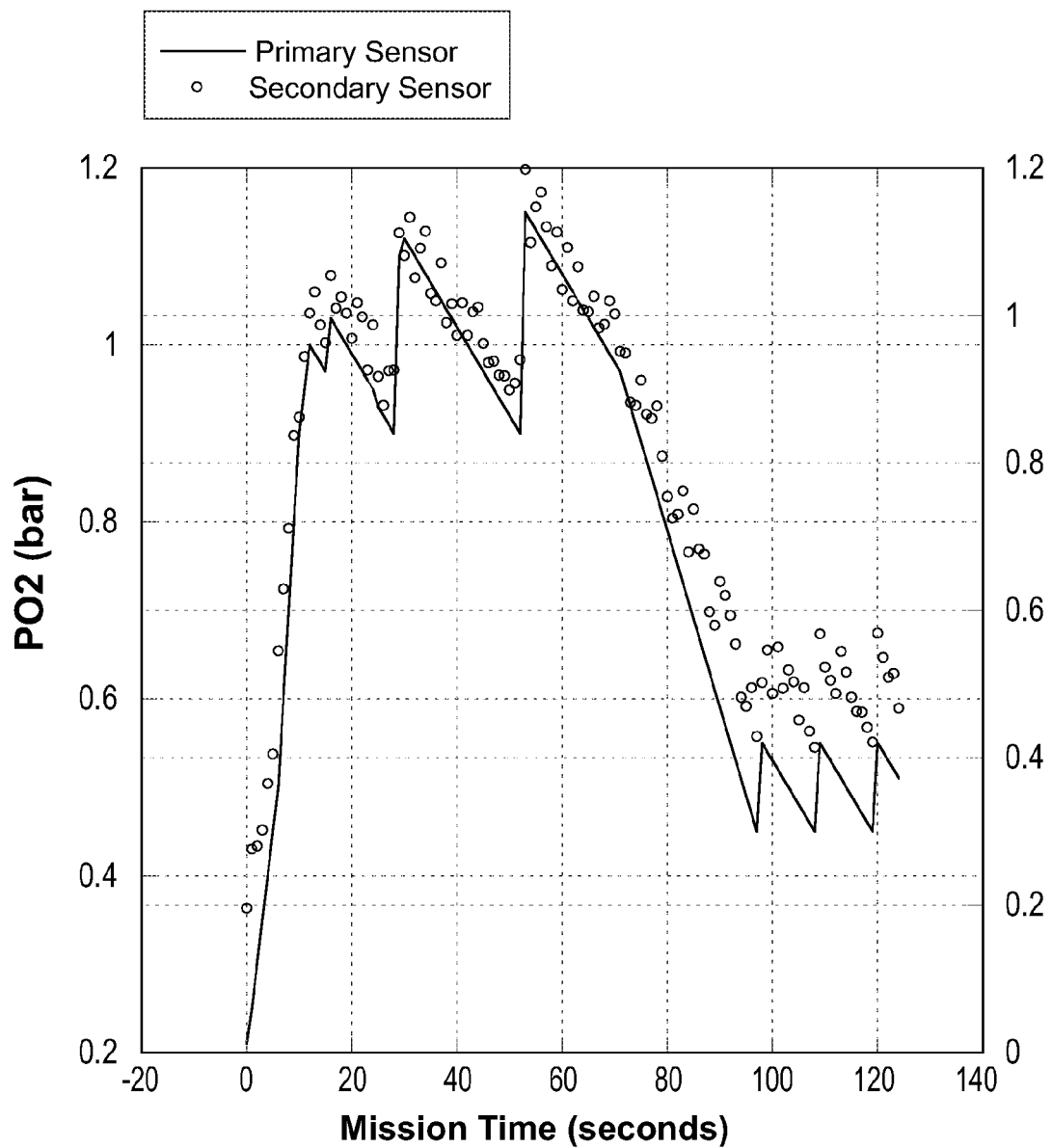
FIG. 10 is a schematic illustration of exemplifying actual mission readings obtained from primary and secondary oxygen sensor during a descent.

An example of a realistic mission is presented in FIG. 10 in which a dive is conducted to a specified operating depth and the control unit 40 attempts to maintain a PO2 of approximately 1.1 bar from approximately T=20 minutes to T=60 minutes. At that point (≈T=60 minutes), an ascent is begun and the control unit 40 attempts to maintain a PO2 of 0.5 bar from approximately T=100 minutes through the end of the mission at approximately T=130 minutes. The circles plotted in FIG. 10 represent the PO2 readings of the secondary sensor 31; the solid line represents the PO2 readings of the primary sensor 30.

In a third step S3" of the exemplifying method illustrated in FIG. 3d it is preferred that calibration curve is obtained for the secondary oxygen sensor 31 by using at least the majority of the readings obtained in the previous step S2" just described above.

Since the PO2 readings for the primary sensor 30 are known to be good (at least after a successful validation as described above with reference to FIG. 3c), it is then possible to compute a regression curve (i.e. the transfer function) or similar between the primary oxygen sensor 30 and the secondary oxygen sensor 31 respectively to obtain a corrected calibration curve for the secondary sensor 31.

Figure 9:
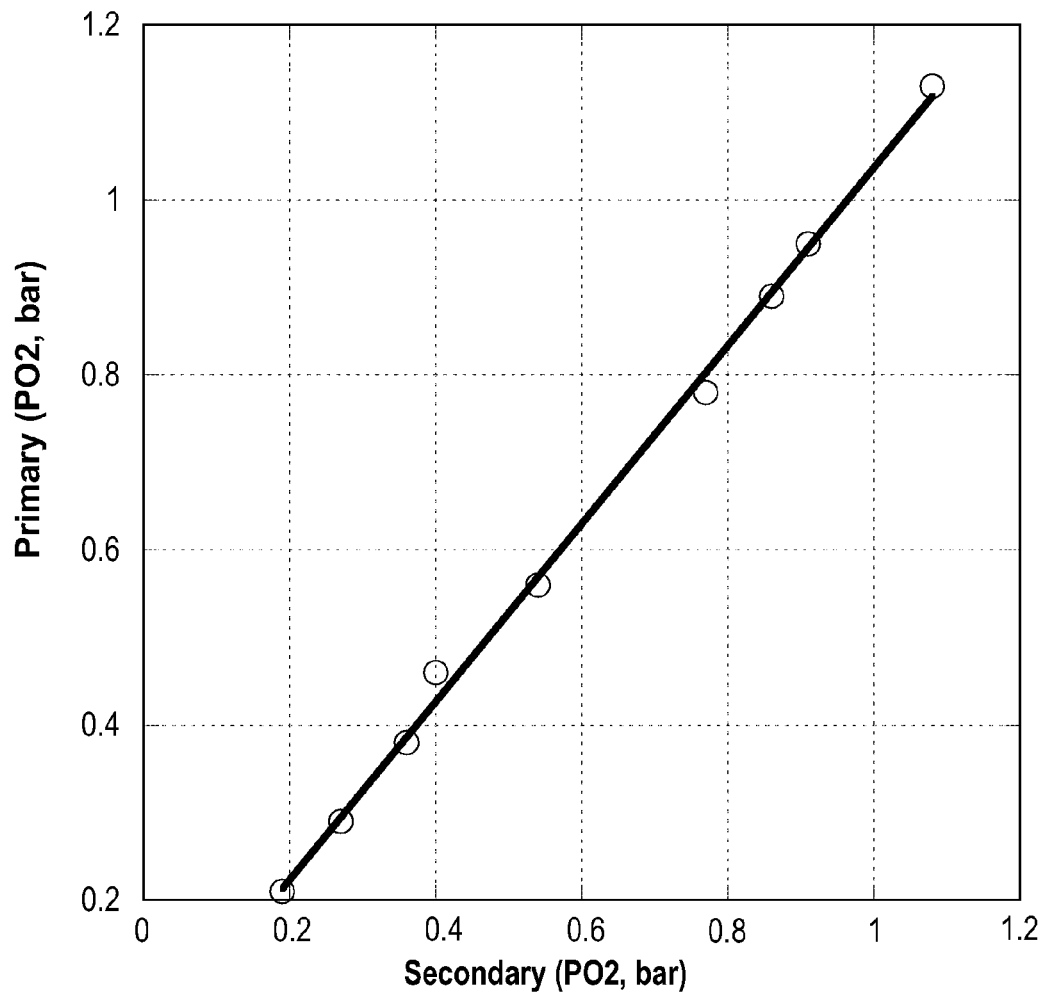
FIG. 9 is a schematic illustration of a linear curve fitted to exemplifying readings from the primary and secondary oxygen sensors during a descent.

For the exemplifying readings from oxygen sensors 30, 31 shown in FIG. 8, a transfer function (i.e. a calibration curve) can be created as shown in the diagram of FIG. 9. The transfer function is shown as a linear fitted curve, i.e. a linear regression equation of the form Y=b+aX is fitted. However, other fitted curves are clearly conceivable, e.g. other polynomial curves or other curve types as various conic sections etc. The "X" (horizontal) axis of the graph in FIG. 9 represents the PO2 readings of the secondary sensor 31 while the "Y" (vertical) axis represents the PO2 readings of the primary sensor 30.

As already indicated above, the data shown in FIGS. 8 and 9 are simplistic and the method described above is valid across substantially all possible closed-cycle breathing apparatus mission profiles. This applies mutatis mutandis for other breathing apparatuses.

Figure 11:
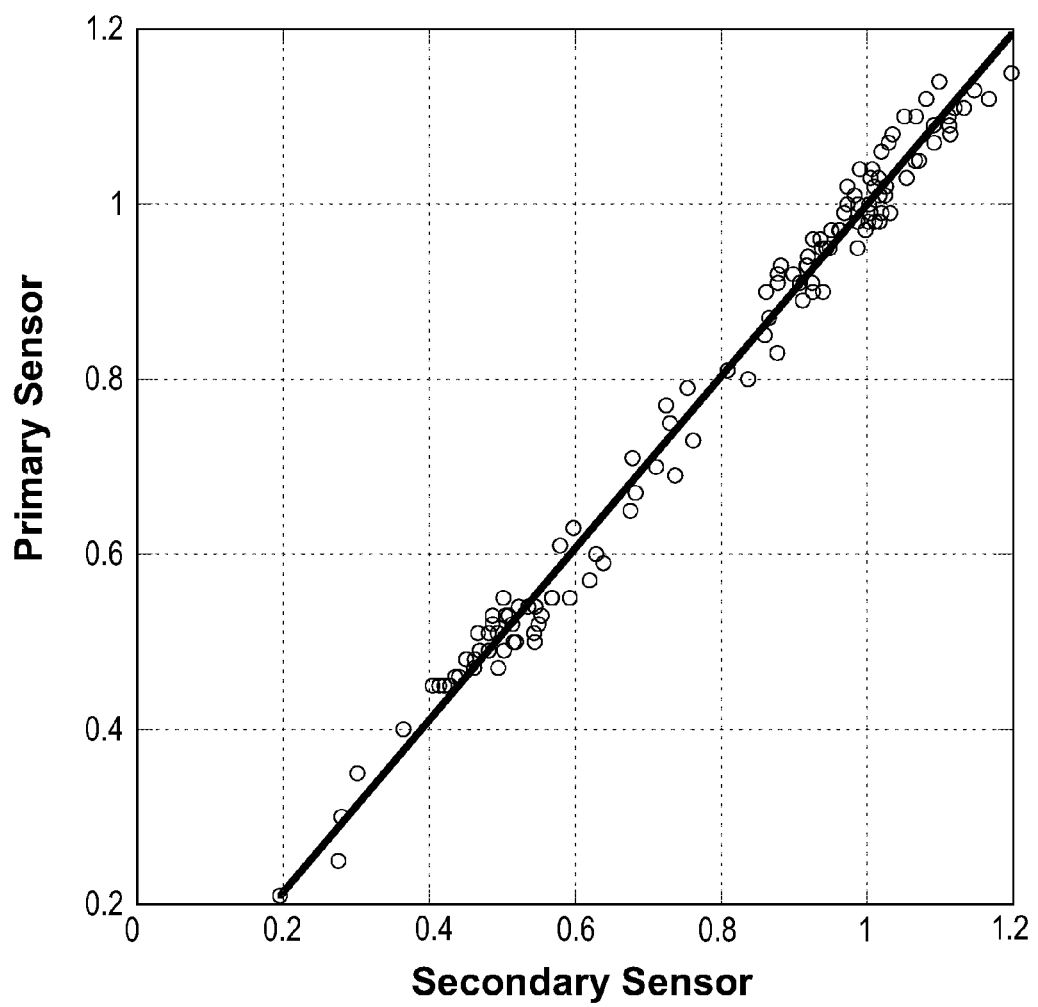
FIG. 11 is a schematic illustration of a linear curve fitted to the readings from primary and secondary oxygen sensors during the mission shown in FIG. 10.

An example of a more realistic mission is presented in FIG. 10, as described above. For this data set a realistic linear transfer function Y=b+aX for the secondary sensor 31 can be fitted to the readings. This is shown in the graph of FIG. 11, which again plots on the X (horizontal) axis the readings of the secondary sensor 31 and on the Y (vertical) axis the readings of the primary sensor 30. To use the transfer function of FIG. 11, the secondary sensor value is entered into the "X" variable in the equation and the "Y" result is the corrected PO2 value.

In a fourth step S4" of the exemplifying method illustrated in FIG. 3d it is preferred that a number of checks to ensure that the method now described uses quality data.

This may e.g. include:

Validating the primary sensor 30 as described above with reference to FIG. 3c before and after a regression table is generated, so that there exists a high degree of confidence that the primary readings are valid.

Standard statistical techniques such as computing the regression coefficient and rejecting transfer function curves with a coefficient outside acceptable tolerance limits.

Preferably a statistical correlation value or a similar representation—e.g. an R value or an $R^2$ value—corresponding to the correlation of the oxygen sensors readings with respect to the fitted curve is obtained. This is preferably accomplished by calculation utilising the oxygen sensors readings obtained in step S2" and the fitted calibration curve obtain in step S3". The statistical correlation value can be then compared to an allowable tolerance. The allowable tolerance may e.g. be a predetermined value or range or similar. A predetermined value or range or similar may e.g. be obtained by empirical investigations or similar.

If the statistical value is outside the allowable tolerance, i.e. if the degree of fit is sufficiently bad, then the method proceeds to step S5'" and the control unit 40 will issue an alert signal to the user. The alert may have the form of an advisory warning message or an abort message.

Otherwise, the secondary sensor 31 now uses the corrected calibration curve defined by the fitted curve, e.g. defined by a linear transfer function Y=b+aX as described above. The secondary sensor 31 can then be relied upon for emergency guidance to the control unit 40 in the event that the primary sensor 30 is determined (e.g. from failure of a periodic nonlinearity check) to have failed (provided that the transfer function was generated prior to the non-linear failure of the primary oxygen sensor, a state that, as described above, is capable of being exactly determined through the methods presented herein).

The method now described is a powerful diagnostic tool providing a automated method for auto-calibrating the secondary sensor 31.

One very common failure mode in CCR type operations, because they operate in very humid environments, is the formation of condensate on the oxygen sensor sensing surface. When this happens it is common for the sensor readings for the affected sensor to "freeze" in their state of output at the time of formation of the condensation on the sensing surface. In existing CCR systems it is impossible to detect this automatically with any reliability because it is unknown which sensors are affected, and therefore what can be used as a ground truth against which to reliably detect a condensate-saturated sensor. With the method presented herein it is possible to directly detect secondary sensor condensation (the primary sensors are already cleared of condensate and independently validated through the methods described above.

Figure 12:
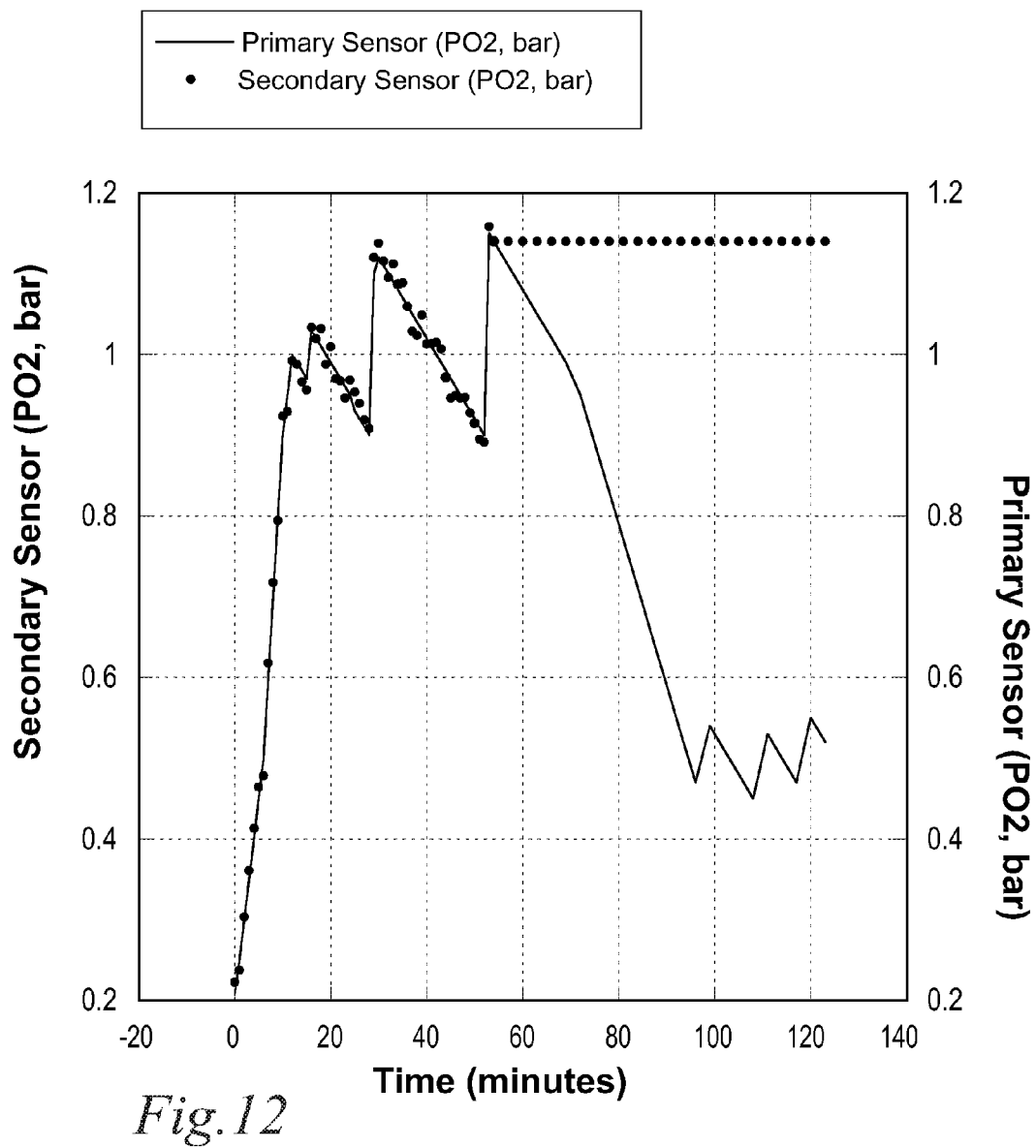
FIG. 12 is a schematic illustration similar to the one in FIG. 10, except that the secondary sensor 31 has a condensate film formed on its sensing surface at T=50.

FIG. 12 shows a normal mission dive profile, similar to FIG. 10, except that at approximately T=55 minutes the secondary sensor 31 has a condensate film form on its sensing surface, freezing the output from the secondary sensor 31 at a PO2 level of 1.14 bar, which persists throughout the remainder of the mission.

Figure 13:
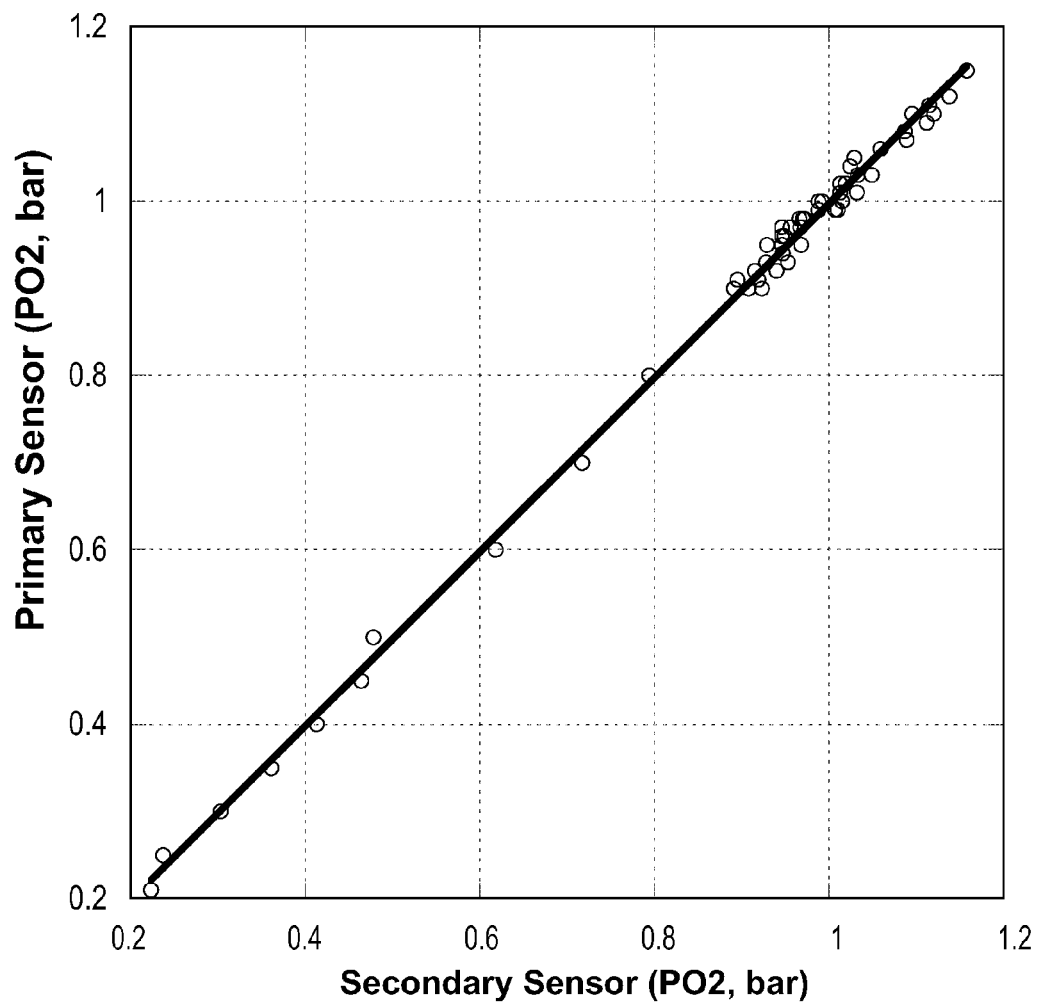
FIG. 13 is a schematic illustration of a linear curve fitted to the readings from primary and secondary oxygen sensors to T=55 during the mission shown in FIG. 12.
Figure 14:
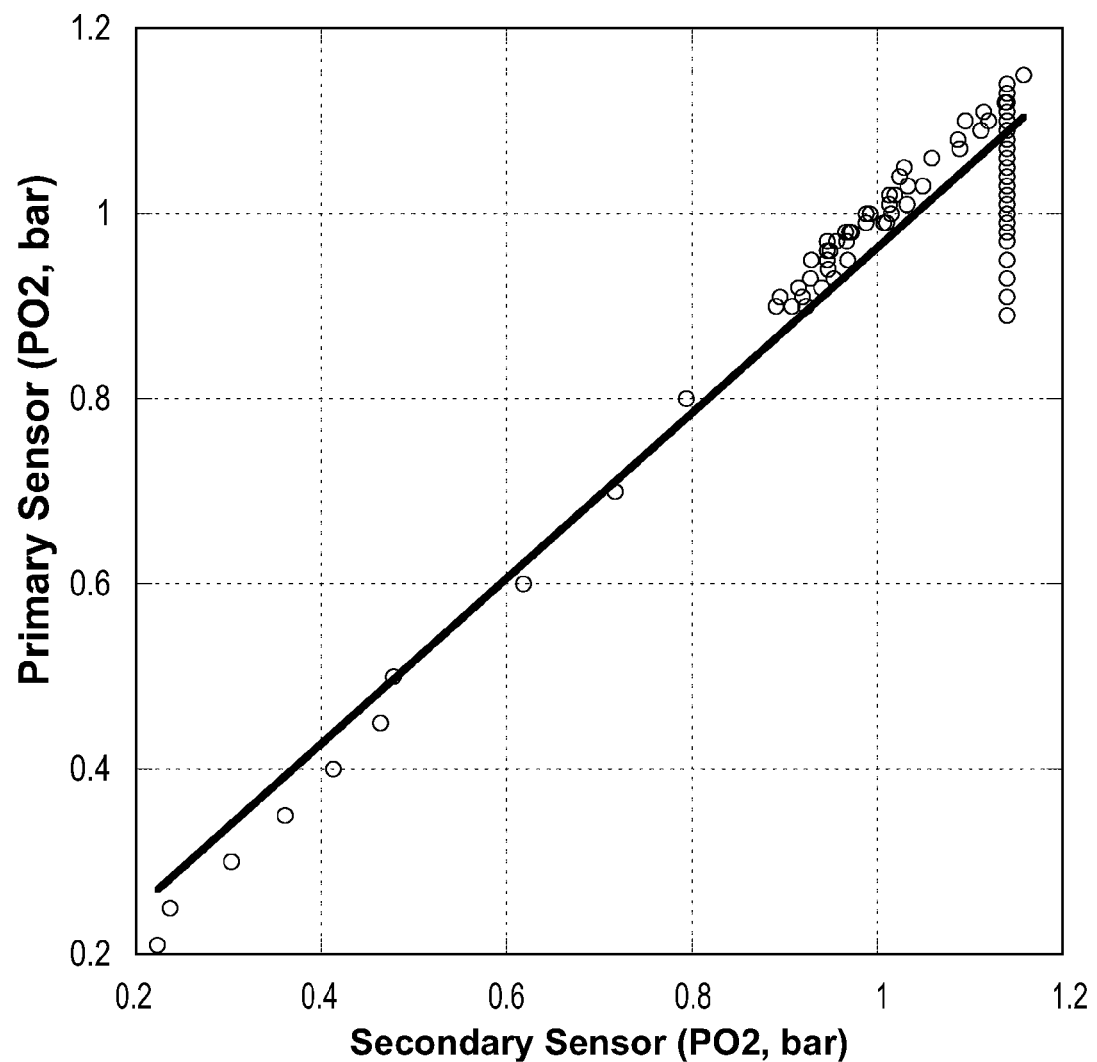
FIG. 14 is a schematic illustration of a linear curve fitted to the readings from primary and secondary oxygen sensors to T=75 during the mission shown in FIG. 12
Figure 15:
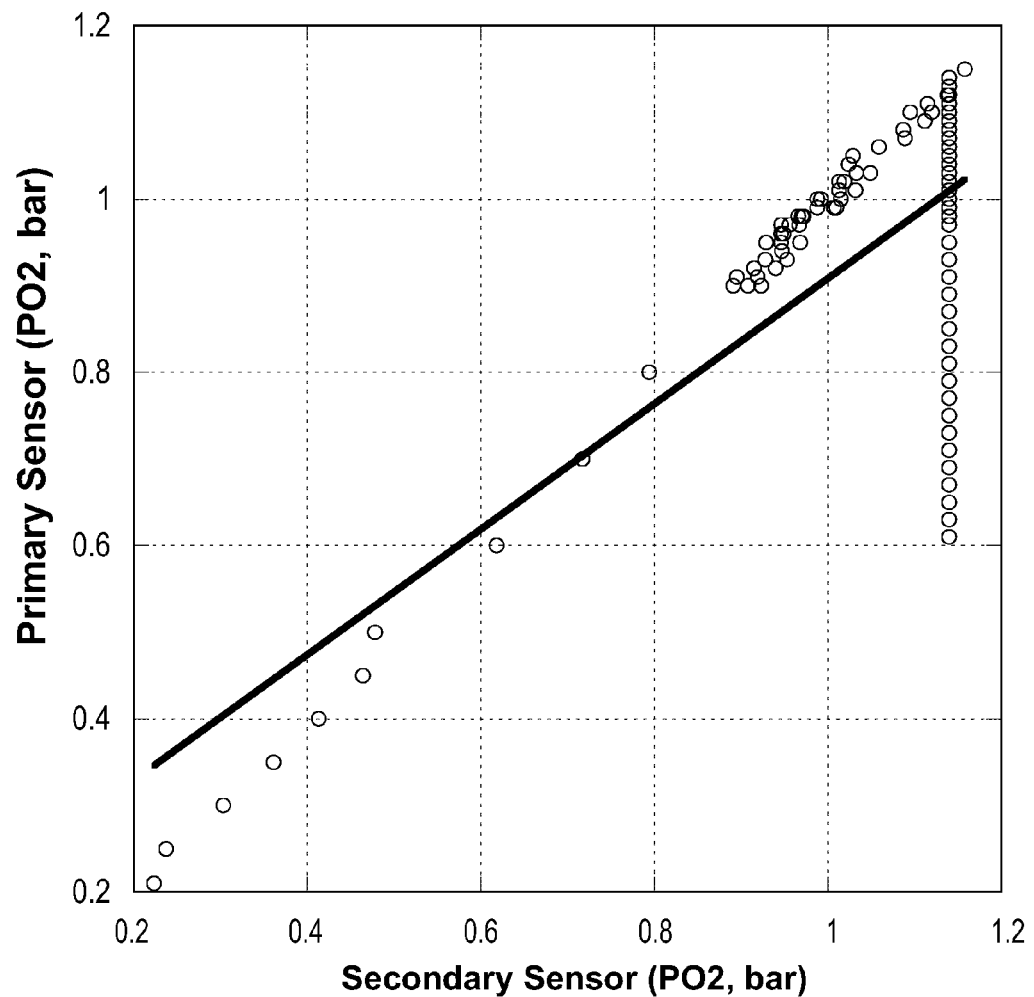
FIG. 15 is a schematic illustration of a linear curve fitted to the readings from primary and secondary oxygen sensors to T=100 during the mission shown in FIG. 12
Figure 16:
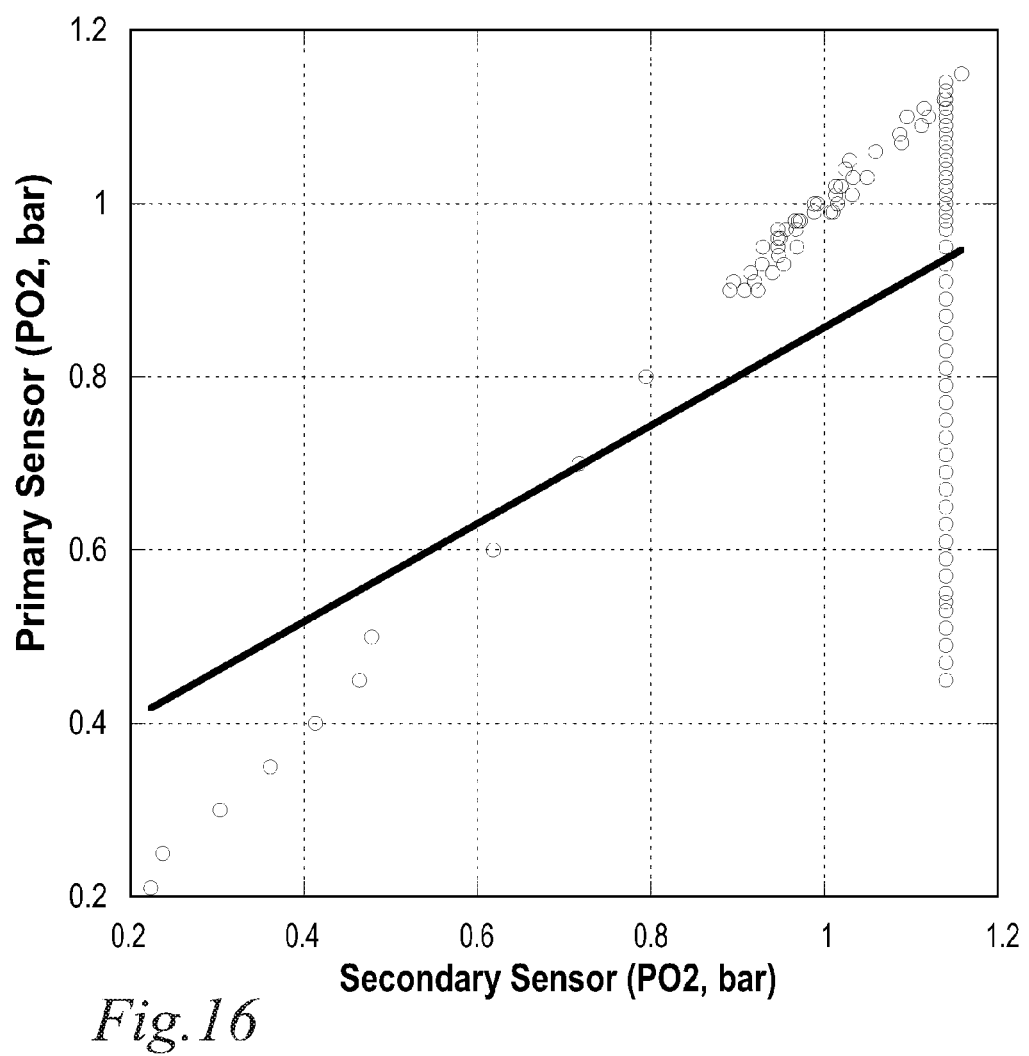
FIG. 16 is a schematic illustration of a linear curve fitted to the readings from primary and secondary oxygen sensors to T=130 during the mission shown in FIG. 12

From the beginning of the mission and up through approximately T=55 minutes, the secondary sensor transfer function is linear with excellent statistical fit, as shown in FIG. 13. However, as we proceed beyond T=55 minutes, we see the quantitative result on the transfer function fit (R or $R^2$ value) at T=75 minutes in FIG. 14; at T=100 minutes in FIG. 15 and at T=130 minutes in FIG. 16.

Early detection and rejection of the secondary sensor 31 is possible by setting the threshold tolerance on the degradation of the R or $R^2$ value to a sufficiently small number while maintaining a reasonable tolerance to allow for minor aging effects. With this, we have a powerful suite of diagnostic tools that a relatively simple and compact system (e.g. a CCR using 2 sensors, one of which is directly auto-calibrated) can use for reliable operation and control of PO2 in the system.

Auto Validation of Secondary Sensor(s)

This method employs all of the techniques described above. The control unit 40 maintains a running transfer (regression) curve for each secondary oxygen sensor based upon some arbitrary time period of prior readings (e.g. the last 120 seconds etc). For example, in the Oxygen Sensor Arrangement 8 shown in FIG. 3a this will allow for quick detection if the primary oxygen sensor 30 and secondary oxygen sensor 31 are starting to diverge by means of the historical variation of the regression correlation coefficient (e.g. R or $R^2$).

If statistically significant divergence is detected, then an obvious question is which sensor is correct? Fortunately, this is easily solved as a result of invoking the auto-validation procedure for the primary oxygen sensor 30 as describe above with reference to FIG. 3c, e.g. with a reading every few minutes. If the primary sensor 30 is shown to be good, then the divergence should be attributed to the secondary sensor 31. Conversely, if the primary sensor 30 is shown to be in error, then there exists a high degree of confidence that the secondary sensor 31 is working correctly. This method of cross-sensor auto-validation extends to any number of sensors working within the same breathing loop in a closed-cycle life support system.

The present invention has now been described with reference to exemplifying embodiments. However, the invention is not limited to the embodiments described herein. On the contrary, the full extent of the invention is only determined by the scope of the appended claims.

The invention claimed is:

1. A method in an oxygen sensor arrangement for sensing the oxygen in a breathing loop of a breathing apparatus, comprising the steps of:
    actuating a first test valve arrangement so as to provide an amount of a first gas having a first fraction of oxygen via a test channel arrangement to a primary oxygen sensor at a position adjacent to or directly adjacent to said primary oxygen sensor,
    wherein said primary oxygen sensor is arranged in a cavity that is in fluid communication with the breathing loop; and
    wherein said cavity is provided with at least one output orifice for the test channel arrangement arranged at a position adjacent to or directly adjacent to said primary oxygen sensor.

2. The method according to claim 1, wherein the method further comprises:
    actuating a second test valve arrangement so as to provide an amount of a second gas having a second fraction of oxygen via said test channel arrangement to said primary oxygen sensor at a position adjacent to or directly adjacent to said primary oxygen sensor.

3. The method according to claim 2, wherein the method further comprises:
    obtaining at least one second test measure from said primary oxygen sensor when it is provided with an amount of said second gas.

4. The method according to claim 3, wherein the method further comprises:
    calculating at least a first calibration point using said first test measure and at least using the known fraction of oxygen in the first gas,
    calculating at least a second calibration point using said second test measure and at least using the known fraction of oxygen in the second gas, and
    generating a calibration curve for said primary oxygen sensor at least based on said first calibration point and said second calibration point.

5. The method according to claim 3, wherein the method further comprises:
    obtaining a validation point value using said first test measure or said second test measure,
    obtaining an expected value for the validation point value, at least using the known fraction of oxygen in the first gas or the known fraction of oxygen in the second gas, and
    determining if the validation point value deviates from the expected value more than a predetermined amount.

6. The method according to claim 5, wherein the method further comprises:
    obtaining the expected value for the validation point value by using the calibration curve so as to compensate for possible deviations in said primary oxygen sensor.

7. The method according to claim 3, wherein the method further comprises:
    obtaining a measure of ambient pressure from a pressure sensor in connection with at least one of said first test measure or said second test measure, so as to provide a partial pressure of oxygen for at least one of said first test measure or said second test measure.

8. The method according to claim 2, wherein the method further comprises:
   injecting said first gas or said second gas at an oblique angle with respect to the surface of the primary oxygen sensor.

9. The method according to claim 1, wherein the method further comprises:
   obtaining at least one first test measure from said primary oxygen sensor when it is provided with an amount of said first gas.

10. The method according to claim 1, wherein the method further comprises:
    obtaining measures from the secondary oxygen sensor and the primary sensor when no test valve arrangements are actuated to provide any of the first gas or the second gas onto the secondary oxygen sensor or the primary sensor.

11. The method according to claim 10, wherein the method further comprises:
    obtaining a fitted calibration curve for said secondary oxygen sensor using measures operatively assembled from the secondary oxygen sensor and the primary sensor.

12. The method according to claim 11, wherein the method further comprises:
    obtaining statistical correlation representation indicative of the correlation of the assembled measures with respect to the obtained fitted calibration curve.

13. The method according to claim 12, wherein the method further comprises:
    issuing an alert to the user if the statistical correlation representation is outside an allowable tolerance.

14. The method according to claim 10, wherein the method further comprises:
    actuating at least one of said first test valve arrangement or said second test valve arrangement if the primary sensor measures deviates from the secondary oxygen sensor measures more than a predetermined amount.

15. The method according to claim 10, wherein the method further comprises:
    arranging the secondary oxygen sensor at a distance from the gas output of at least one of said first test valve arrangement or said second test valve arrangement, such that a gas leakage from at least one of said first test valve arrangement or said second test valve arrangement will cause the secondary sensor to operatively provide a different measure compared to the measure provided by the primary oxygen sensor.

* * * * *